United States Patent [19]
Roth et al.

[11] Patent Number: 5,990,388
[45] Date of Patent: Nov. 23, 1999

[54] RESISTANCE TO VIRUSES AND VIROIDS IN TRANSGENIC PLANTS AND ANIMALS EXPRESSING DSRNA-BINDING PROTEIN

[75] Inventors: Don Allen Roth; Jeffrey Olaf Langland, both of Laramie, Wyo.

[73] Assignee: Research Corporation Technologies, Inc., Tucson, Ariz.

[21] Appl. No.: 08/482,286

[22] Filed: Jun. 7, 1995

[51] Int. Cl.$^6$ ............ C12N 5/00; C12N 15/00; A01H 1/04
[52] U.S. Cl. ............ 800/301; 800/280; 800/317.2; 800/317.3; 435/320.1; 935/64
[58] Field of Search ............ 800/205, 280, 800/301, 317.2, 317.3; 435/172.3; 935/64

[56] References Cited

U.S. PATENT DOCUMENTS

| | | | |
|---|---|---|---|
| 5,252,479 | 11/1993 | Srivastava | 435/235.1 |
| 5,324,643 | 6/1994 | Greatbatch et al. | 435/91.32 |
| 5,399,346 | 3/1995 | Anderson et al. | 424/93.21 |

OTHER PUBLICATIONS

Anderson, W. French, "Prospects for Human Gene Therapy," *Science* (1984) 226:401–409.
Chang, H–W and Jacobs, B.L., "Identification of a Conserved Motif That Is Necessary for Binding of the Vaccinia Virus E3L Gene Products to Double–Stranded RNA," *Virology* (1993) 194:537–547.
Chang, H–W et al., "E3L gene of vaccinia virus encodes an inhibitor of the interferon–induced, double–stranded RNA–dependent protein kinase," *Proc. Natl. Acad. Sci. USA* (1992) 89:4825–4829.
Fitchen, J.H. and Beachy, R.N., "Genetically Engineered Protection Against Viruses in Transgenic Plants," *Annu. Rev. Microbiol.* (1993) 47:739–63.
Langland, J.O. et al., "Identification of a Plant–Encoded Analog of PKR, the Mammalian–Double–Stranded RNA–Dependent Protein Kinase," *Plant Physiol* (1995) 108:1–9.
Langland, J.O. et al., "Nucleic Acid Affinity Chromatography: Preparation and Characterization of Double–Stranded RNA Agarose," *Protein Expression and Purification* (1995) 6:25–32.
Langland, J.O. et al., "Products of the Porcine Group C. Rotavirus NSP3 Gene Bind Specifically to Double–Stranded RNA and Inhibit Activation of the Interferon–Induced Protein Kinase PKR," *J. Virology* (1994) 68(6):3821–3829.
Miki, B.L. et al., "Procedures for Introducing Foreign DNA into Plants," CRC Press, Inc. (1993) pp. 67–80.
Nelson, R.S. et al., "Virus Tolerance, Plant Growth, and Field Performance of Transgenic Tomato Plants Expressing Coat Protein from Tobacco Mosaic Virus," *Biotechnology* (1988) 5:403–409.
Qian, Y. et al., "Molecular Analysis of the Gene 6 from a Porcine Group C Rotavirus That Encodes the NS34 Equivalent of Group A Rotaviruses," *Virology* (1991) 134:752–757.
St. Johnston, D. et al., "A conserved double–stranded RNA–binding domain," *Proc. Natl. Acad. Sci. USA* (1992) 89:10979–10983.
Tolstoshev, P. and Anderson, W.F., "Gene Transfer Techniques for Use in Human Gene Therapy," *Genome Research in Molecular Medicine and Virology*, Academic Press, Inc. (1993) pp. 35–50.
JD Watson et al. (1987) Molecular Biology of the Gene p. 313.
E Beattie et al. (1995) J Virology 69:499–505.
Y Devash et al. (1982) Science 216: 1415–1416.
K Lee et al (1996) Mol Cell Biol 16: 3023–3034.
EF Meurs et al. (1995) Virology 214:653–659.
JK Lodge et al. (1993) Proc Natl Acad Sci USA 90: 7089–7093.

*Primary Examiner*—Bruce R. Campell
*Attorney, Agent, or Firm*—Greenlee, Winner & Sullivan, P.C.

[57] ABSTRACT

The invention provides a method for imparting resistance in animals to viruses, and in plants to viruses and viroids, that express double-stranded RNA-like structures (dsRNAs). This method enables the binding of pathogenic dsRNAs during the infection process by expression of dsRNA-binding protein in transgenic animal and plant hosts, thus interrupting the infection cycle and inhibiting disease. The presence of a dsRNA-binding protein in a transgenic host renders the transgenic host resistant to the phenotypic symptoms of viral infection and/or decreased pathogen replication. Accordingly, the present invention provides a genetically engineered animal and plant, stably transformed to express a dsRNA-binding protein, such that the transgenic host displays resistance to virus and/or viroid challenge.

18 Claims, 7 Drawing Sheets

RESISTANCE TO VIRUSES AND VIROIDS IN TRANSGENIC PLANTS AND ANIMALS EXPRESSING DSRNA-BINDING PROTEIN

The invention was partially made with Government support under Grant, No. MCB9220617 awarded by the National Science Foundation, Grant No. 348445 awarded by the Wyoming Agricultural Experimental Station and Cooperative Agreement No. SCA 58-5354-5-705 awarded by the United States Department of Agriculture.

FIELD OF THE INVENTION

The invention relates generally to genetic engineering and, more particularly, to a means and method for imparting resistance from viral and viroid infection to a plant or animal host expressing double-stranded RNA binding protein. Such engineered human cells may be used in gene therapy.

BACKGROUND OF THE INVENTION

Many agriculturally important crops are subject to infection by plant viruses and viroids. These viruses can seriously damage a crop and drastically reduce its economic value to the grower. This eventually leads to a higher cost of the goods to the ultimate consumer. Attempts to control or prevent infection of a crop by a plant virus have been made, but until recently none have been completely satisfactory. Accurate global figures for crop losses due to viruses alone are not available. However, some idea of the scale can be obtained by considering that plant disease losses worldwide were estimated to be in excess of $60 billion per year in 1986.

Human and animal diseases associated with viral infections present a continuing challenge for development of new products, treatments and therapies. A fresh approach in the treatment of infectious diseases arose from demonstration of the ability to successfully introduce foreign genes into eukaryotic cells. Gene therapy, which is the introduction of genetic material into mammalian somatic cells in order to treat malignant, infectious or inborn genetic diseases, is considered to be a realistic and desired method of treatment for viral-induced infections, including malignancies.

One of the most important goals today is the development of virus resistant plants and animals. Current methods for viral protection involve the use of a virus component to stimulate an antiviral state in the host. Such protection appears not to be broad, but specific to related species. Plants or animals exhibiting broad spectrum viral resistance are not available.

The theory of virus-derived resistance proposes that pathogen resistance genes can be derived from a pathogen's own genetic material. Numerous examples of virus-resistance have been reported for many different plant RNA viruses in a wide range of plant species. Most examples of virus-resistance involve transgenic plants engineered to express a viral coat protein (CP) or a segment of a replicase gene (for reviews, see Beachy et al., Ann. Rev. Phytopathol. 28:451–474; Wilson, 1993, Proc. Natl. Acad. Sci. 90:3134–3141). As a general rule, transgenic plants accumulating one of these viral proteins are often resistant to that particular virus and closely related viruses. For example, the coat protein (CP) of the protectant virus was thought to be primarily responsible, either by preventing particle disassembly or by re-encapsidating the incoming genome of the more severe challenge virus. However, viroids [240- to 380-nucleotides-long, naked circular single-stranded RNA (ssRNA) pathogens] and mutant viruses making assembly-defective or no detectable CP could also cross-protect against their more severe relatives. Although many examples of virus resistance have been documented, in general, the mechanism(s) underlying resistance remains to be clearly defined.

Although plant transformations with viral coat protein sequences, partial replicase gene sequences, antisense RNA sequences to key viral genes, and satellite viruses have resulted in moderate levels of disease resistance highly specific to only certain host-virus interactions, problems related to recombination of viral genes inserted into hosts have increased the biohazard potential of these approaches. To our knowledge, there is no viable strategy to develop viroid resistant plants.

There exists, therefore, a continuing need for an improved method and effective means for controlling virus- and viroid-infection in plants and animals, and for providing transgenic species that are broadly resistant to multiple viruses and viroids.

The interferon system is the primary host defense against viral infection in vertebrates [Lengyel (1982) Ann. Rev. Biochem. 51:251–282]. It is thought that dsRNA, which is produced during most viral infections, can act as an inducer for interferon synthesis [Field et al. (1967) Proc. Natl. Acad. Sci 58:1004–1010]. Once synthesized, interferons are secreted, bind to specific receptors on cells, and induce an antiviral state. Cells in the antiviral state are more resistant to infection by most viruses. Several interferon-induced enzymes are involved in the establishment of the antiviral state. One of the interferon-induced enzymes is the $P_1$/eIF-$2\alpha$ protein kinase that can autophosphorylate and phosphorylate exogenous substrates including the eukaryotic protein synthesis initiation factor eIF-2, and histone proteins [Samuel et al. (1986) Meth. Enzymol. 119:499–516; Jacobs and Imani (1988) J. Interferon Res. 8:821–830]. Autophosphorylation and activation of the $P_1$/eIF-$2\alpha$ kinase requires binding to dsRNA [Galabru and Hovanessian (1987) J. Biol. Chem. 262:15538–15544]. Once activated, the $P_1$/eIF-$2\alpha$ kinase can phosphorylate eIF-2 on its a subunit and alter the interaction of eIF-2 with the GDP/GTP exchange factor eIF-2B, leading to an inhibition of protein synthesis [Safer (1983) Cell 33:7–8].

A number of viruses, including adenovirus, influenza virus, human immunodeficiency virus type 1, reovirus, Epstein-Barr virus, and vaccinia virus have been reported to produce or induce inhibitors of the $P_1$/eIF-$2\alpha$ kinase [Kitajewski et al. (1986) Mol. Cell. Biol. 6:4493–4498; Lee et al. (1990) Proc. Natl. Acad. Sci. 87:6208–6212; Gunnery et al. (1990) Proc. Natl. Acad. Sci. 87:8687–8691; Imani and Jacobs (1988) Proc. Natl. Acad. Sci 85:7887–7891; Clarke et al. (1990) Eur. J. Biochem. 193:635–641; Whitaker-Dowling and Younger (1983) Virology 131:128–136; Paez and Esteban (1984) Virology 134:12–28; and Rice and Kerr (1984) J. Virol. 50:229–236] and consequently evade one of the antiviral modes of interferons. For example, large quantities of VAI RNA are produced in adenovirus-infected cells. The VAI RNA can bind to the $P_1$/eIF-$2\alpha$ kinase and prevent its activation [Galabru et al (1989) Eur. J. Biochem. 178:581–589]. For reovirus, a dsRNA binding protein, σ3, functions as the $P_1$/eIF-$2\alpha$ kinase inhibitor by binding to and competing for activator dsRNA (Imani and Jacobs 1988, supra). In the case of influenza virus, the kinase inhibitor is a cellular protein activated during viral infection (Lee et al. 1990, supra). Adenovirus and certain strains of reovirus have been demonstrated to be resistant to the antiviral effects of interferon [Kitajewski et al. (1986) supra; Jacobs and Ferguson (1991) J. Virol 65:5102–5104]. For adenovirus, deletion of the gene for VAI RNA leaves the virus interferon sensitive (Kitajewski et al. 1986, supra).

Replication of vaccinia virus in mouse L cells is resistant to interferon treatment [Younger et al. (1972) J. Virol. 10:171–180]. Vaccinia virus infection can also rescue other viruses, such as vesicular stomatitis virus (VSV) and encephalomycarditis virus (EMCV) (Whitaker-Dowling and Younger, 1983, supra; 1986, Virology 152:50–57] from the anti-viral effects of interferon. The primary effect of interferon-treatment on VSV replication is an inhibition of the translation of viral mRNA [Samuel (1988) Prog. Nucl. Acid Res. Mol. Biol. 35:27–72]. However, when coinfected with vaccinia, translation of VSV mRNA was rescued (Whitaker-Dowling and Younger, 1983, supra; 1986, supra). It has been suggested that the vaccinia virus inhibitor of the interferon-induced $P_1$/eIF-2α kinase may partly contribute to the interferon resistance of vaccinia virus and to the rescue of VSV and EMCV from the antiviral effects of interferon.

To date, several dsRNA binding proteins have been identified, including the human and mouse interferon-induced, dsRNA-dependent protein kinases (PKR) [Meurs et al. (1990) Cell 62:379–390; Icely et al. (1991) J. Biol. Chem. 266:16073–16077, respectively]; a human transactivator response element/Rev response element binding protein (TAR/RRE) [Gatignol et al. (1991) Science 251:1597–1600]; the vaccinia virus p25 protein [Ahn et al. (1990) Mol. Cell Biol. 10:5433–5441]; *Escherichia coli* RNase III protein [March et al. (1985) Nucl. Acids Res. 13:4677–4685]; the Drosophila staufen gene product [St. Johnston et al. (1991) Cell 66:51–63]; the *Saccharomyces pombe* PacI protein [Ilino et al. (1991) EMBO J. 10:221–226]; Xenopus RNA-binding protein A [St. Johnston et al. (1993) Proc. Natl. Acad. Sci. 89:10979–10983]; the human son-a protein [St. Johnston et al. (1992) Proc. Natl. Acad. Sci. 89:10979–10983]; reovirus σ3 protein [Imani et al. (1988) Proc. Natl. Acad. Sci. 85:7887–7891]; and the porcine group C rotavirus NSP3 and p8 proteins [Langland et al. (1994) J. Virol 68:3821–3829]. Genes for these dsRNA binding proteins share homology in a region at the C terminus [Chang et al. (1993) Virology 194:537–547; St. Johnston et al. (1992) Proc. Natl. Acad. Sci. 89:10979–10983] having the dsRNA-binding domain consensus sequence:

R/K-E-F-X-X-G/A-X-G-R/K-S-T-K-R-K/R-E/D-A-K-N/Q-A-A-A-K-L-V/V-A-L/V-D/E (SEQ ID NO: 1).

Retroviruses are the causative agents for an increasing number of diseases of higher organisms including: AIDS, HIV, various leukemias, feline leukemia, murine leukemia, several avian leukemias, various sarcomas of mice, rats, monkeys, birds, and cats, and other lymphotrophic diseases of man, including Adult T-Cell leukemia. Acquired Immune Deficiency Syndrome (AIDS), the recently most noteworthy of these diseases, is caused by a retrovirus which has been called HTLV-III, LAV, RAV or most recently HIV [Coffin et al. (1986) Science, 232:697]. HIV is one of a group of retroviral diseases which attacks the T4 lymphocytes thereby destroying the body's immune system [Anderson, (1984) Science 226:401–409; Weiss (1985) *In RNA Tumor Viruses-II*, Vol. 2, Cold Spring Harbor Laboratory, pp. 405–485]. The disease is uniformly fatal and no cure has been developed which either kills the virus in situ or replaces the lost elements of the body's immune system. Some experimental drugs show limited effects in stopping the virus, but to date there is no proven therapy or cure for the AIDS patient. The high mutation rate resulting in a wide variation in antigenicity of various strains of the virus makes it unlikely that a traditional vaccine for the virus will be developed soon.

Retroviral diseases differ from many other viral diseases in that the infective agent, a retrovirus, eventually becomes integrated in the host cell's genome. The retrovirus inserts its genome into a host chromosome, such that its genetic material becomes part of the genetic makeup of the infected cell and is then replicated with the cell as the cell divides and multiplies. It is this characteristic which makes retroviruses especially persistent and immune to traditional anti-viral treatment. There is as yet no way to kill the retrovirus without killing the host cell. Thus, there is no proven cure, nor is there any proven effective vaccine or pharmacological agent against any retroviral disease.

Details of the life cycle and replication of retroviruses are discussed in Weiss et al., *RNA Tumor Viruses*, vols. 1 and 2 (Cold Springs Harbor Laboratory 1984), which is incorporated herein by reference in its entirety. FIG. 1 summarizes a model of a retrovirus life cycle. The life cycle of retroviruses is unique among viruses. The cycle begins when an infectious particle enters a host cell and releases two identical RNA molecules. These molecules are "reverse transcribed" by special viral enzymes to produce double-stranded DNA which circularizes and inserts into the host chromosome. The inserted DNA virus or "pro-virus" is structurally very similar to a normal host gene. It is transcribed to produce RNA, like any host gene. This RNA can then be processed in three ways: (a) it can be directly translated into certain viral proteins; (b) it can be processed and spliced, and then translated to produce other viral proteins; or (c) it can be packaged, along with various viral proteins to make a newly infectious particle. In the case of HIV, the infectious particles continuously "bud off" the infected cells and bind to uninfected cells, beginning the cycle over again.

The retroviral particle which is the infectious agent contains in its interior two single-stranded positive-sense viral RNA molecules each between 7,000 to 11,000 nucleotide bases in length. These viral RNAs combine with certain viral proteins to form a viral core, the core being surrounded by a membrane. Imbedded in the membrane are viral glycoproteins which can specifically bind the viral particles to the appropriate host cell system. The viral core is assembled within the host cell and exits from the host cell, taking some of the host's membrane with it. Hence the membrane of the viral particle is derived directly from the host cell. The particle travels to an uninfected host cell, and due to the glycoprotein on its exterior binds to the new host cell and the life cycle repeats. Once the virus enters the cell, it is disassembled, releasing the two identical viral RNA molecules. These molecules are each composed of a sequence having specific functional regions making up the virus' "genomic structure."

The genome of any retrovirus is divided into three regions: the 5' terminus, the 3' terminus and a central region containing genes coding for proteins (see FIG. 2). The 5' terminus is further divided into four functional regions: the terminal redundancy (R), a unique sequence (U5), the primer binding site (PB- or PBS) and an untranslated sequence (L). The L region may contain a splice donor site for subgenomic mRNA. The 3' terminus is further divided into three functional regions: the primer-binding site for positive strand DNA synthesis (PB+ or PBS), a unique sequence (U3) and another copy of the terminal redundancy (R). The U5, U3 and R regions are sometimes collectively referred to as the long Terminal Repeat (LTR) region. Components of the LTR region are involved in integration of the retroviral genome into the genome of its host. All retroviruses contain these highly conserved regions.

The production of DNA from the infectious RNA occurs by a complex process called reverse transcription. The viral reverse transcriptase enzyme first complexes with a specific tRNA molecule supplied by the host cell. For example, in the case of the AIDS-related virus, it is lysine tRNA which complexes with the reverse transcriptase. The 3' end of the tRNA molecule remains free to hybridize with the primer binding site (PBS) of the retroviral genome. This is a sequence within the virus, which is complementary to the 5' end of the tRNA. Once the virus enzyme tRNA complex has been formed, the enzyme can make a new DNA molecule, using the RNA virus as a template, and using the tRNA as a "primer." As the process proceeds, the RNA of the resulting RNA/DNA complex is degraded, leaving single-stranded DNA. While reverse transcription continues, second-strand DNA synthesis beings from the poly-purine site upstream of the U3 region and continues in the opposite direction from the first-strand DNA synthesis. The RNA primer molecule is consequently degraded. The DNA genomic structure differs from the RNA genomic structure in having a redundant U3 region added to the 5' end, and a redundant U5 region added to the 3' end. This genomic structure resembles a normal gene, with U3 being the promoter, with structural genes in the center, and a U5 tail.

The exact process of how the DNA virus inserts into host chromosomes is not known. It is known that the DNA virus first becomes a circle, and that this involves the short inverted repeat sequences at the ends of the virus. These inverted repeats may be involved in some form of DNA hybridization which brings the ends of the virus together, allowing circularization. Subsequently, insertion into the chromosome is generally assumed to be mediated by an enzyme which recognizes the splice site in the circle and directs insertion of a single copy of the virus into a random site within the host chromosome.

The transcription of viral DNA from the DNA pro-virus within a chromosome occurs in a manner similar to the transcription of any host gene. The U3 region functions as a polymerase II promoter and transcription begins at the beginning of the R region. The U3 promoter, like eukaryotic promoters, generally requires a transcriptional activator protein, which turns the promoter "on." Transcription proceeds through most of the pro-virus and is terminated at the end of the 3' R region. As a result, the transcript is a recreation of the smaller and infectious single-strand RNA genome. A poly-A tail is attached to the 3' end of this RNA and the 5' end is capped, making this molecule similar to normal host messenger RNA.

The RNA which is transcribed from DNA can be directly translated into protein, like any mRNA within the host. Some viral RNA is not translated into protein but rather is packaged into infectious viral particles. Such packaging involves the binding of certain viral proteins to specific sequences of the viral genome. For example, in the RSV viral system, it is part of the GAG sequence which is one of the parts of the genome which binds to and is recognized by such proteins and have been shown to be necessary for packaging of the RNA. The RNA which is packaged into viral particles does not appear to be reverse-transcription-competent until "maturation" of the particle, i.e., after it has existed away from the host cell.

All retroviruses, including HIV, once inserted into the host chromosome, must have their genes translated into viral proteins. If viral proteins are not abundant, the retrovirus cannot efficiently propagate to other cells and is not cytopathic to the infected host cell [Dayton et al. (1986) Cell 44:941–947; Fisher et al. (1986) Nature 320:367–371]. Such proteins are not produced without the proper functioning of certain viral regulatory proteins. One of the key DNA/RNA-binding regulatory proteins for the retrovirus HIV is the TAT protein [Keegan et al. (1986) Science 231:699–704]. The TAT protein is essential to protein translation of HIV, and possibly also involved in RNA transcription. It is apparent that the TAT protein recognizes and binds to the nucleic acid sequence corresponding to the 5' end of the R region. A second activator gene ART has also been shown to be important in HIV translation [Sodroski et al. (1986) Nature 321:412–417]. DNA/RNA binding of the previously described activator proteins is essential to HIV replication. Therefore, introducing genes into host cells, i.e., gene therapy for humans or germline transformation for animals, which will code for modified proteins of the retrovirus which compete or interfere with TAT or ART, will effectively block retrovirus replication.

Past research efforts have been predominantly confined to two traditional anti-retroviral approaches: immunological prevention and pharmacological therapy, neither of which appear to be very promising for control of retrovirus diseases. Also, chemical repression of virus diseases has not generally been effective in eradicating any persistent virus, and certainly would not be expected to eradicate a retrovirus. Anti-viral chemicals tend to slow the progress of a virus and to bolster native defense mechanisms, but chemical treatments must be continuously applied and typically have undesirable side effects.

For these reasons, it is doubtful that any retroviral disease can be cured by the traditional anti-viral approaches. An alternative approach to inhibiting retrovirus replication is genetic inhibition by introducing antisense constructs into host cells (gene therapy).

In the field of human medicine, altering the genotype of the host has not been a desirable method of fighting infectious disease. However, it is now believed that gene therapy is the direction now and for the relative future [Anderson (1984) Science 226:401–409]. There are many pathogens for which conventional defenses appear inadequate, and where the use of RNA replication inhibitors might be feasible. Many of the cells that are infected by retroviruses are derived from hematopoietic stem cells. If these stem cells can be altered by the incorporation of genes or other nucleic acid sequences which will synthesize RNA inhibitors that are antagonistic to virus propagation, an efficient method to both effectively prevent and to treat these retroviral diseases will be apparent. Further, if the expression of the RNA replication inhibitors can be regulated in the desired cells, it has application to other genetic diseases.

It would therefore be desirable to provide methods and compositions for expression inhibitors of RNA replication which are particularly effective at the dsRNA-like structure of the TAT site.

SUMMARY OF THE INVENTION

The invention provides a method for the development of broad resistance in animals to viruses and in plants to viruses and viroids. This method is founded upon the binding of pathogen double-stranded RNA-like structures (dsRNAs) during the infection process by specific dsRNA-binding proteins expressed in transgenic hosts. Since virtually all viruses and viroids have a replication phase in which dsRNA or a dsRNA-like structure is present in the cytoplasm of the infected cell, the expression of a dsRNA-binding protein in a transgenic host enables sequestration of the pathogenic dsRNA-like structure, interrupting the infection cycle and inhibiting disease. The presence of a dsRNA-binding protein in a transgenic host renders the transgenic host resistant to the phenotypic symptoms of viral infection and/or decreased pathogen replication. One or more dsRNA proteins may be expressed in a transgenic host.

Accordingly, the present invention provides a genetically engineered animal and plant, stably transformed to express constitutively a dsRNA-binding protein, such that the transgenic host displays resistance to virus and/or viroid challenge. One aspect of the invention contemplates broad spectrum resistance in transgenic plant cells to plant viruses having a dsRNA-like structure, including but not limited to the phytoreovirus group, the tymovirus group, luteovirus group, tombusvirus group, Southern bean mosaic virus group, tobacco necrosis virus group, maize chlorotic dwarf virus group, closterovirus group, carlavirus group, potyvirus group, potexvirus group, tobamovirus group, nepovirus group, pea enation mosaic virus group, comovirus group, tobravirus group, cucumovirus group, bromovirus group, ilarvirus group, alfalfa mosaic virus group, and hordeivirus group; and to plant viroids having a dsRNA-like structure, including but not limited to the potato spindle tuber viroid, the coconut cadang-cadang viroid group, avocado sunblotch viroid group, and hop latent viroid group.

In specific embodiments, agriculturally-important plants, including but not limited to tobacco, potato and tomato, are stably transformed with a gene encoding a dsRNA-binding protein, E3L, from vaccinia virus. E3L protein binds to dsRNA-like structures in a virtually irreversible manner. The E3L protein is expressed constitutively in the transgenic plants. E3L transgenic tobacco plants exhibit high resistance to tobacco mosaic virus (TMV) challenge.

In another embodiment of the invention, agriculturally important plants are stably transformed with a gene encoding a dsRNA-binding protein, P8, from a group C rotavirus. The P8 protein is expressed constitutively in transgenic plants. Essentially the entire protein is involved in binding dsRNA.

In accordance with the aforementioned embodiments, the invention provides a genetically engineered plant, including but not limited to tobacco, potato and tomato, stably transformed with a gene encoding E3L or P8 protein, such that a dsRNA-binding protein, E3L or P8 protein, is expressed constitutively and such that the transgenic plant exhibits resistance to infection and disease by any virus or viroid having a dsRNA-like structure.

In other embodiments, mammalian cells, including but not limited to mouse L cells, HeLa cells and COS cells, are transformed with a gene encoding a dsRNA-binding protein, vaccinia E3L protein or rotavirus group C P8 protein. The dsRNA-binding protein is constitutively expressed in the transformed mammalian cell, and is made available to bind dsRNA-like structures which participate in critical viral processes, e.g., replication. The presence of dsRNA-binding protein acts to protect against viral infections. The invention contemplates broad spectrum resistance in transgenic animals including humans, from viruses having a dsRNA-like structure, including but not limited to the picornavirus group, togavirus group, bunyavirus group, ilantaan virus group, arcnavirus group, rhabdovirus group, orthomyxovirus group, paramyxovirus group, coronavirus group, hepatitis delta group and retrovirus group.

In another embodiment of the invention, animals, including humans, are transformed with a gene encoding a dsRNA-binding protein, such as the vaccinia E3L protein, the rotavirus P8 protein, etc. Expression of dsRNA-binding protein in transgenic animals allows sequestration of the viral dsRNA-like structure necessary for vital viral processes. In a particular embodiment, a gene encoding a dsRNA-binding protein is introduced using a retroviral vector system into a human, such that the dsRNA-binding protein is expressed in an amount sufficient to confer in the human resistance to infection from viruses having a dsRNA-like structure.

The present invention further provides utility for dsRNA binding proteins as regulatory molecules in in vivo and in vitro systems comprising an obligatory or critical dsRNA-like structure for functionality, as occurs in systems such as viral/viroid pathogenesis, cell division, transcriptional activation, protein translation, cancer and tumor development, non-cancer diseases and other such applications. It is contemplated that the dsRNA-binding protein expressed in a host binds dsRNA-like structures with high affinity such that the transgenic host is rendered resistant to any virus having a dsRNA-like structure.

Accordingly, the invention contemplates the use of dsRNA-binding proteins having high affinity for dsRNA to scavenge and effectively remove the dsRNA-like structure from participating in critical viral processes. The dsRNA-binding proteins provided by this invention comprise a dsRNA-binding domain having the consensus sequence of R/K-E-F-X-X-G/A-X-G-R/K-S-T-K/R-K/R-E/D-A-K-N/ Q-A-A-A-K-L/V-A-L/V-D/E (SEQ ID NO: 1).

[Chang et al. (1993) Virology 194:537–547]. Proteins that are chemically synthesized or biochemically modified to comprise the dsRNA-binding domain consensus sequence are also contemplated by the invention. Such dsRNA-binding proteins are found in viral, prokaryotic and eukaryotic sources, including but not limited to the human and mouse interferon-induced, dsRNA-dependent protein kinases; the vaccinia virus E3L protein; *Escherichia coli* RNase III protein; the human TAR/RRE binding protein; the Drosophila staufen gene product; the *Saccharomyces pombe* Pac1 protein; Xenopus RNA-binding protein A; porcine rotavirus group C P8 protein; the reovirus σ3 protein; and the human son-a protein.

In another aspect of the invention, methods are provided to measure the level of viral or viroid infection in a host cell, utilizing either an antiserum to dsRNA-binding protein or an assay for dsRNA-like structure-dsRNA-binding protein complex formation in a host cell.

Further, the invention provides a method of gene therapy for a human infected with a viral infection where the virus has a dsRNA-like structure. A gene encoding a dsRNA-binding protein is introduced into the patient such that a therapeutically effective amount of dsRNA-binding protein is expressed, allowing the patient to develop resistance against any virus having a critical dsRNA-like structure. In a specific embodiment, the dsRNA-binding protein gene is introduced into the patient with a retroviral vector. In another specific embodiment, the patient receiving gene therapy and expressing dsRNA-binding protein acquires resistance to a human immuno-deficiency virus.

BRIEF DESCRIPTION OF THE FIGURES

FIG. 4A–4B present the effect of E3L protein expression on TMV replication. Total protein extracts were prepared from transgenic tobacco plants expressing the E3L gene (isolate 10-1) (lane A), the glycine-valine mutated E3L gene (isolate 2A-1) (lane B), the parental vector pBIN-19 (isolate 13A-2), or the host plant (Samsun nn) (lane D). In Part A, plants were infected with tobacco mosaic virus (TMV). In part B, plants were left uninfected. Proteins were separated by SDS-PAGE, transferred to nitrocellulose and probed with antibody to the TMV coat protein. The position of the coat protein is indicated by the asterisk. Molecular weight markers (kDaltons) are indicated.

FIG. 5 presents transgenic tobacco (Samsun nn) plants transformed with E3L and a nonfunctional mutant.

FIG. 6 presents an enlargement of the phenotypic response.

FIG. 7 presents the interaction of the TAR RNA molecule with the HIV-1 TAT protein and a 68 kdalton cellular protein. The TAT protein binds to the region around the three-base bulge at position 23–25, while the cellular protein binds to the loop at the top of the TAR hairpin.

FIG. 8 presents schematically the participation of dsRNA-like structure in interferon-induced activation cycles, i.e., the 2-50AS/RNase L and dsRNA-dependent protein kinase pathway. In this figure, INF=interferon and 2-5OAS=2'5' oligoadenylate synthase.

DETAILED DESCRIPTION OF THE PREFERRED EMBODIMENTS

The following definitions are given in order to provide clarity as to the intent or scope of their usage in the specification and claims.

The term a recombinant DNA molecule or a recombinant RNA molecule or a recombinant nucleic acid molecule, as used herein, refers to a DNA or RNA molecule which does not occur in nature; i.e., it is produced either by natural processes using methods known to the art, but is directed by man to produce a desired result, or it has been artificially produced from parts derived from heterologous sources, which parts may be naturally occurring or chemically synthesized molecules or portions thereof, and wherein those parts have been joined by ligation or other means known to the art.

The term transgenic plant or transgenic animal, as used herein, refers to a plant or animal which has been genetically modified to contain and express heterologous DNA. As specifically exemplified herein, a transgenic plant or animal is genetically modified to contain and express a virus- or viroid-resistance phenotype that is not normally present in the plant or animal host. As further used herein, a transgenic plant or animal also refers to progeny of the initial transgenic plant or animal, which progeny carry and are capable of expressing the virus- or viroid-resistance phenotype. Seeds containing transgenic embryo are encompassed within this definition. As used herein, a transgenic plant is a monocotyledonous or a dicotyledonous plant. In a preferred embodiment of the present invention the transgenic plant is tobacco, rice, wheat, barley, maize, tomato, cucumber, soya, sweet potato, grapes, rapeseed, sugar beet, cotton, tea, sunflower, strawberry, rose, chrysanthemum, sweet pepper or potato. As used herein, a transgenic animal includes but is not limited to a pet animal, a farm animal, a domesticated animal, a game animal, a wild animal and a human.

The term virus as used herein refers to an entity that: (a) contains a single type of nucleic acid, either DNA or RNA; (b) contains a protein coat (sometimes enclosed by an envelope of lipids, proteins and carbohydrates) that surrounds the nucleic acid; (c) multiplies inside living cells using the synthesizing machinery of the cell; and (d) causes the synthesis of specialized elements that can transfer the viral nucleic acid to other cells. Plant viruses cause many diseases of economically important crops, including tomatoes (e.g., Tomato Mosaic Virus), corn (Maize dwarf mosaic virus) and sugarcane (e.g., Wound Tumor Virus), and potatoes (e.g., Potato Leaf Roll Virus). Viruses can cause color change, deformed growth, wilting, and stunted growth in their plant hosts. Viruses must enter plant cell walls through wounds or by plant parasites, e.g., nematodes, fungi, insects, etc. Mammalian viruses cause infections and cancers in animals.

The term viroid as used herein refers to a short piece of naked RNA, approximately 300 to 400 nucleotides long, without a protein coat. The nucleotides are often internally paired, so the molecule has a closed, folded, three-dimensional structure to protect against cellular enzymes. Viroids appear to be pathogens only of plants. For example, the Potato Spindle Tuber Viroid (PSTV) is capable of infection and multiplication, without need to be incorporated into a capsid, causing disease in such hosts as potatoes and tomatoes.

The term host range as used herein refers to the spectrum of host cells that the virus can infect. Viruses multiply only in cells of particular species. The particular host range of a virus is determined by the virus' requirements for its specific attachment to the host cell and the availability within the potential host of cellular factors required for viral multiplication. Most viruses have broad host ranges.

The term double-stranded RNA-like structure (dsRNA) as used herein refers to not only an RNA structure comprising two strands of RNA (dsRNA) but also includes the region of a single-stranded RNA having a secondary structure containing a highly base-paired stem loop structure, for example the TAR region of HIV. According to the invention, the presence of a dsRNA-like structure is critical for viral replication.

The term double-stranded RNA-binding protein or dsRNA-binding protein as used herein refers to a protein capable of specifically binding to a dsRNA structure or to the region of a ssRNA having a dsRNA-like structure. Formation of a complex between a dsRNA-binding protein and the dsRNA disrupts a critical viral process such as replication.

The term virus having a dsRNA-like structure as used herein refers to an RNA virus that requires the presence of a dsRNA-like structure for its replication or other critical process in a host cell. Plant virus groups that produce critical or obligatory dsRNA-like structures during pathogenesis and that are susceptible to control via dsRNA-binding proteins include but are not limited to:

Figure 1:
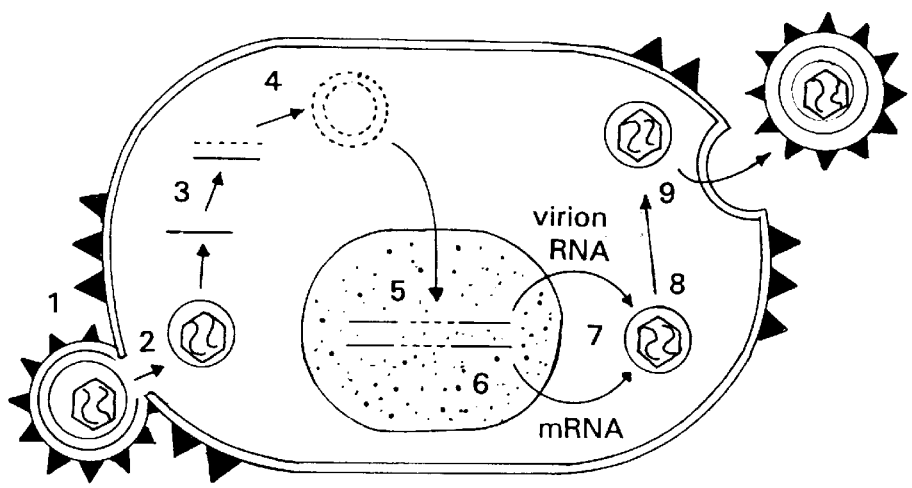
FIG. 1 presents schematically a model of a retrovirus life cycle. In steps 3 to 5 of an HIV infection cycle, the viral core proteins are associated with the viral genome where—refers to RNA and - - - refers to DNA. Double-stranded circular forms can be found both covalently and non-covalently bound. The latter are the forms that integrate into the cell chromosome. Antiviral therapies can be directed against each step and can potentially interrupt virus replication and spread. The steps shown are: (1) attachment and fusion; (2) uncoating and nucleocapsid entry; (3) reverse transcription; (4) cDNA formation; (5) integration; (6) mRNA transcription; (7) translation; (8) core particle assembly; and (9) final assembly and budding. Steps 8 and 9 most probably occur at the cell surface.
Figure 2:
FIG. 2 presents schematically the genome of a retrovirus.
Figure 3:
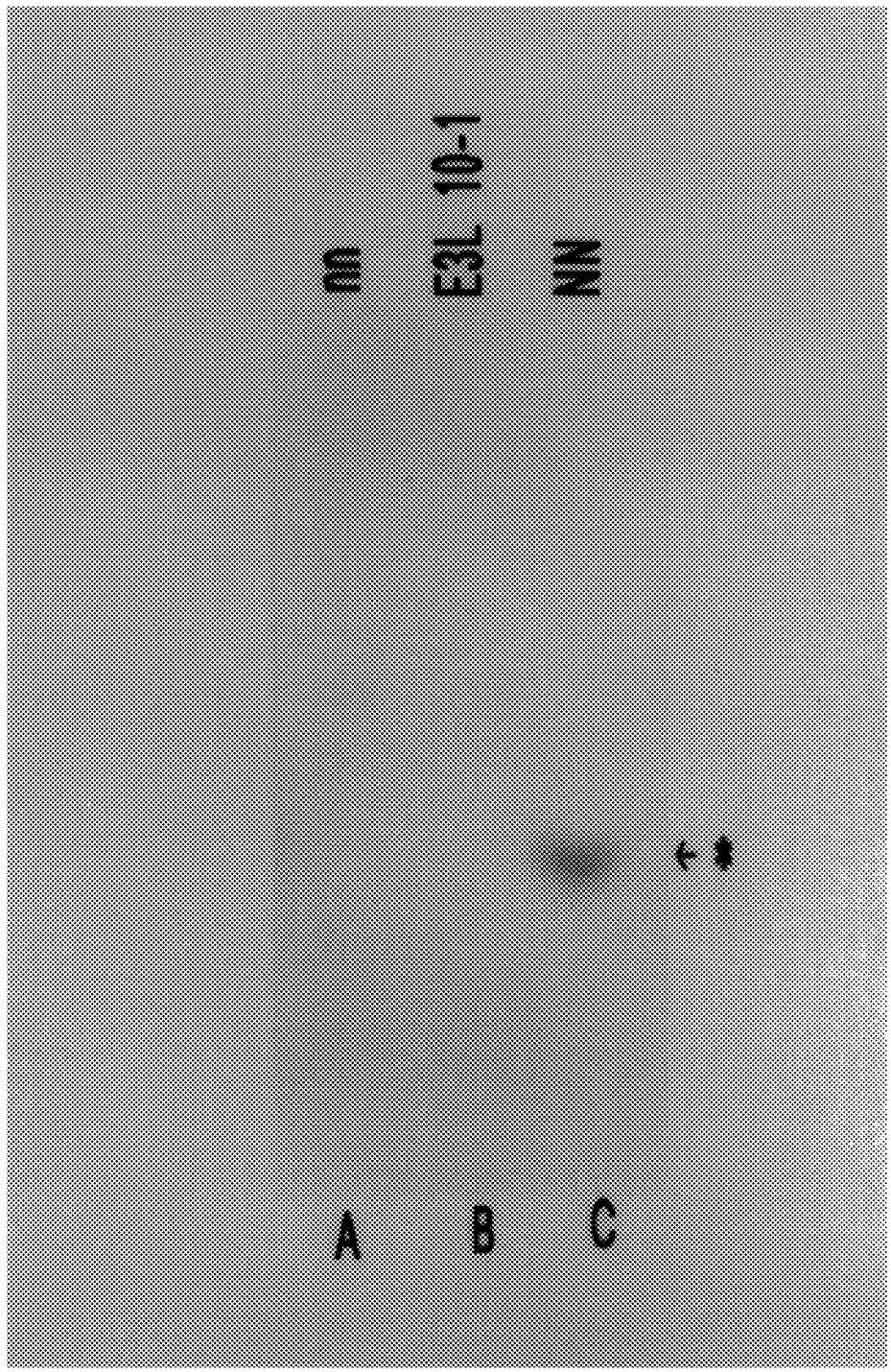
FIG. 3 presents a Southern blot analysis of tobacco plant. Genomic DNA was isolated from Samsun nn (lane A), Samsun nn transformed with the E3L gene (isolate 10-1) (lane B), and Samsun NN (lane C) tobacco plants. DNA was separated on an agarose gel, transferred to nitrocellulose and probed with a radiolabelled probe specific to the Samsun NN strain of tobacco. Hybridized probe was detected by autoradiography. Asterisk indicates the position of the expected band from Samsun NN plants.
Figure 4:
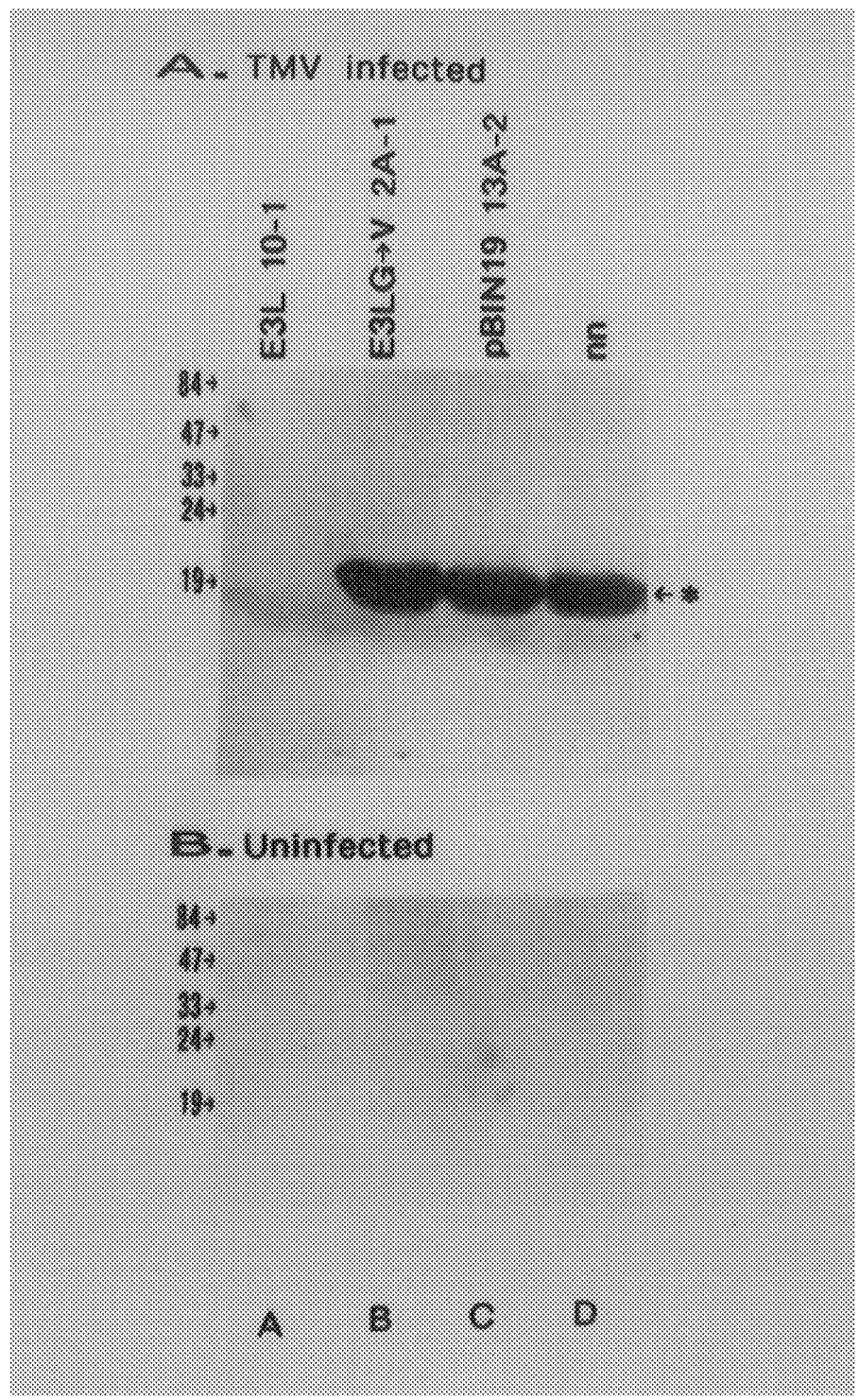
Figure 5:
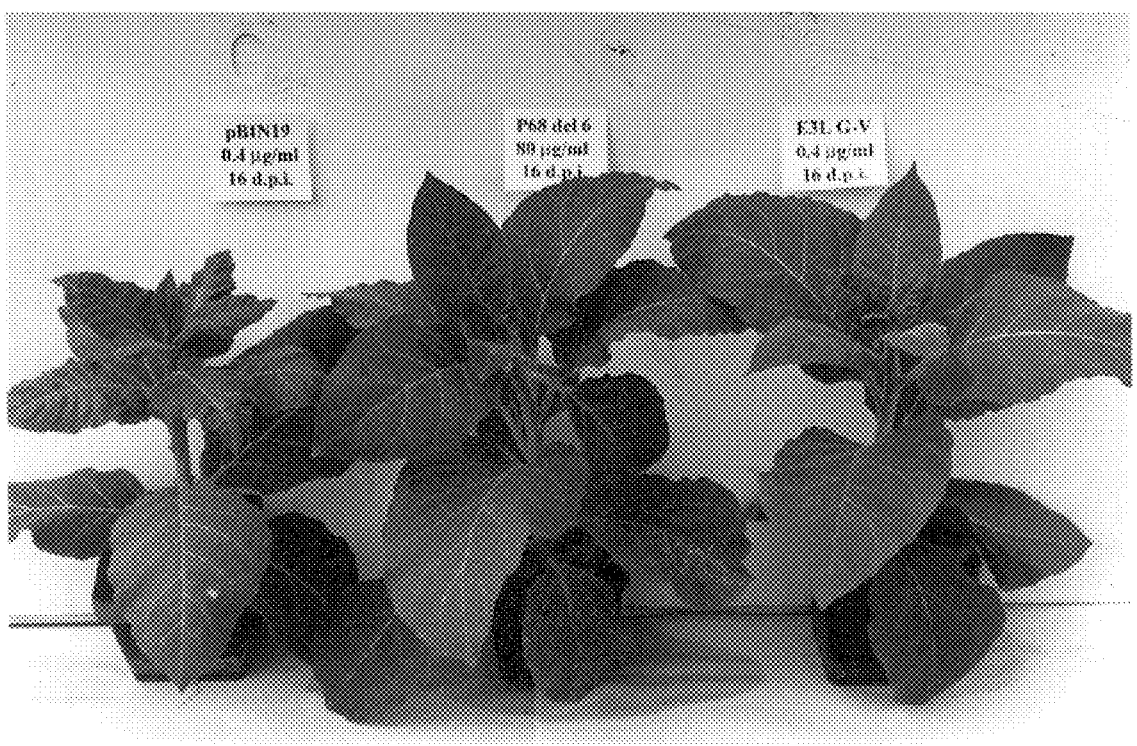
Figure 6:
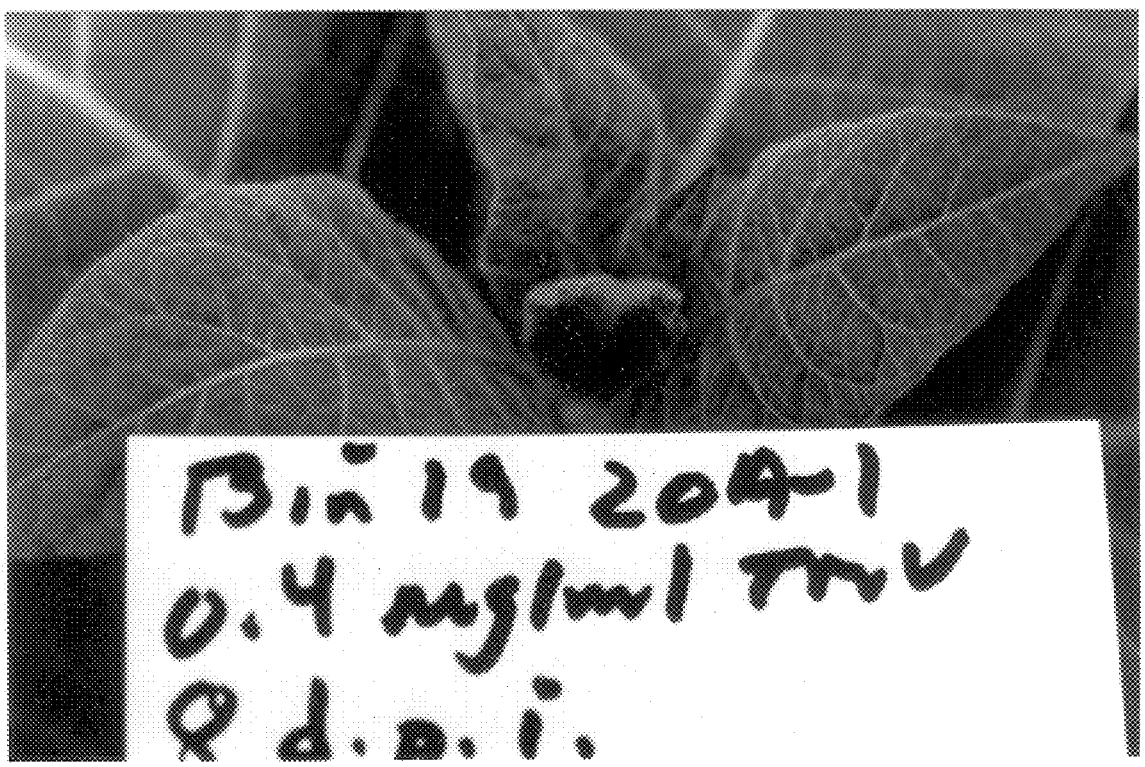

the Phytoreovirus group (dsRNA genome)—[rice dwarf virus, rice dwarf gall virus];

the Tymovirus group (+sense ssRNA genome)—[turnip yellow mosaic virus, eggplant mosaic virus];

the Luteovirus group (+sense ssRNA genome)—[barley yellow dwarf virus, beet western yellows virus];

the Tombusvirus group (+sense ssRNA genome)— [tomato bushy stunt virus];

the Southern bean mosaic virus group (+sense ssRNA genome)—[southern bean mosaic virus, turnip rosette virus];

the Tobacco necrosis virus group (+sense ssRNA genome)—[TNV, cucumber necrosis virus];

the Maize chlorotic dwarf virus group (+sense ssRNA genome)—[MCDV, rice tungro virus];

the Closterovirus group (+sense ssRNA genome)—[beet yellow virus, citrus tristeza virus, clover yellow virus];

the Carlavirus group (+sense ssRNA genome)— [Carnation latent virus, alfalfa latent virus, potato M and S viruses];

the Potyvirus group (+sense ssRNA genome)—[PVY, bean common mosaic virus, beet mosaic virus, lettuce mosaic virus, tulip breaking virus, tobacco etch virus, pea necrosis virus, Papaya ringspot virus, pepper mottle virus];

the Potexvirus group (+sense ssRNA genome)—[PVX, cassava common mosaic virus, hydrangea ringspot virus];

the Tobamovirus group (+sense ssRNA genome)—[TMV, potato mop top virus, wheat soil-borne mosaic virus, tomato mosaic virus];

the Nepovirus group (+sense ssRNA genome)—[tobacco ringspot virus, cherry leafroll virus, cocoa necrosis virus, tomato ringspot virus];

the Pea enation mosaic virus group (+sense ssRNA genome) [PEMV];

the Comovirus group (+sense ssRNA genome) [cowpea mosaic virus, bean pod mottle virus, squash mosaic virus, potato mottle virus];

the Tobravirus group (+sense ssRNA genome)—[tobacco rattle virus];

the Cucumovirus group (+sense ssRNA genome)— [cucumber mosaic virus, peanut stunt virus, tomato aspermy virus];

the Bromovirus group (+sense ssRNA genome)—[brome mosaic virus, cowpea chlorotic mottle virus];

the Ilarvirus group (+sense ssRNA genome)—[tobacco streak virus, citrus leaf rugose virus, apple mosaic virus, hop A and C virus, rose mosaic virus];

the Alfalfa mosaic virus group (+sense ssRNA genome)— [AMV]; and the Hordeivirus group (+sense ss RNA genome)—[barley stripe mosaic virus].

Plant viroids that produce a critical dsRNA phase include but are not limited to:

PSTV group—(PSTV, chrysanthemum stunt viroid, citrus exocortis viroid, hop stunt viroid, tomato apical stunt viroid, tomato plant macho viroid);

CCVd group—(coconut cadang-cadang viroid, coconut tinangaja viroid);

ASBVd group—(avocado sunblotch viroid);

ASSVd group—(apple scar skin viroid, grapevine yellow speckle viroid, grapevine viroid); and
- HLVd group—hop latent viroid.

Mammalian viruses that are susceptible to control by dsRNA binding proteins include but are not limited to:

- Picornavirus group (+sense ssRNA genome)—[enteroviruses (i.e., poliovirus), cardioviruses, rhinoviruses (cold viruses), aphthovirus (foot and mouth disease)];
- Togaviruses (+sense ssRNA genome)—[alphavirus (sindbis virus), flaviruses];
- Bunyaviruses (−sense ss RNA genome);
- Ilantaan viruses (−sense ssRNA genome);
- Arenaviruses (+sense ss RNA genome);
- Rhabdovirus (−sense ssRNA genome);
- Orthomyxovirus (−sense ssRNA genome) [e.g., influenza];
- Paramyxovirus (−sense ssRNA genome) [e.g., sendai];
- Coronavirus (+sense ssRNA genome);
- Hepatitis delta ("viroid-like"); and
- Retroviruses (e.g., HIV).

The term Providing resistance or resistant as used herein refers to the protective effect conferred onto a host against infection by a virus or viroid having a critical dsRNA-like structure as judged by any of the criteria, including but not limited to: (a) absence or reduction lesions characteristic of viral infections; (b) absence or reduction in the level of viral coat protein in the host; (c) absence or reduction in the level of dsRNA in the host; (d) absence or reduction in the number of plaques. A host is deemed to be resistant if the measurable or observable pathogenic effects characterizing virus or viroid infections are absent or reduced.

The term a therapeutically effective amount as used herein refers to the level of dsRNA-binding protein that is sufficient to bind to dsRNA-like structures such that viral replication is reduced or prevented and phenotypic symptoms characteristic of viruses having dsRNA-like structures are reduced or dissipated or prevented. The desired degree of therapeutic effectiveness to be achieved by expression of dsRNA-binding protein depends on factors known to the art, such as strength and specificity of promoters driving and directing gene expression, tolerance of a host, etc. Dosages giving the desired degree of effectiveness are readily ascertained by art-known methods.

The term gene therapy as used herein refers to the introduction of genetic material into mammalian somatic cells in order to treat infectious diseases.

Many of the procedures useful for practicing the present invention, whether or not described herein in detail, are well known to those skilled in the art of Recombinant DNA technology. A detailed description of many of such procedures can be found in Maniatis et al. *Molecular Cloning: A Laboratory Manual*, Cold Spring Harbor Laboratory, Cold Spring Harbor, N.Y. (1982); Kaufman (1987) in Genetic Engineering Principles and Methods, J. K. Setlow, ed., Plenum Press, New York, pp. 155–198; Fitchen et al. (1993) Annu. Rev. Microbiol 47:739–764; Tolstoshev et al. (1993) in *Genomic Research in Molecular Medicine and Viroloagy*, Academic Press, all incorporated herein by reference.

A method is developed for creating transgenic plants and animals with broad spectrum resistance to viruses and viroids. The technology of the invention provides virus and viroid protection without the need for prior knowledge of the species of pathogen involved in the infection process. In contrast, current methods used in the art to confer virus resistance require disclosure of the pathogenic species involved and result in the production of plants and/or animals having resistance that is specific to the particular pathogen and close relatives. Thus, the ability to provide plants and animals with resistance to almost all plant viruses/viroids and animal viruses using the technology of the invention is far superior to existing methods and technologies.

Most plant viruses and viroids are composed of single-stranded RNA, usually of 10,000 nucleotides or less. Despite the diverse genomic structures and compositions of plant viruses and viroids, they all appear to exhibit a common feature of genomic single-stranded RNA with high amounts of dsRNA-like structure (herein referred to as "dsRNA-like structure") or the presence of a double-stranded RNA (dsRNA) produced during replication processes.

The technology of the present invention is founded on the concept that the binding of the dsRNA-like structure during the virus/viroid infection process by a specific dsRNA-binding protein which is constitutively expressed in a transgenic plant would disrupt the replication process and afford protection to plants and animals from all pathogens requiring the presence of a dsRNA-like structure for a vital process, e.g., replication. The ability to express dsRNA binding proteins constitutively in a host provides a means for disrupting viral or viroid replication and, consequently, for providing long-term anti-viral or viroid stability, broad range protection, and reduction in potential biosafety risk. The present invention provides a means for protecting plants from many pathogens by complexing the dsRNA-like structure using a protein molecule having a dsRNA-binding domain that, in nature, is utilized regularly for this function.

Further, the present invention does not necessitate any unusual procedures to transform plants with genes encoding dsRNA-binding proteins. Standard procedures are used to produce stable transgenic plants capable of expressing constitutively a dsRNA binding protein.

Double-stranded RNA-binding proteins and their corresponding genes are known in the art. These proteins comprise a highly conserved region at the C-terminus characterized by a consensus amino acid sequence, R/K-E-F-X-X-G/A-X-G-R/K-S-T-K/R-K/R-E/D-A-K-N/Q-A-A-A-K-L/V-A-L/V-D/E (SEQ ID NO: 1).

that forms a dsRNA binding domain [Chang et al. (1993) Virology 194:537–547].

In a particular exemplification of the invention, plant cells are transformed to express E3L, a 25 kDa dsRNA-binding protein encoded on a vaccinia virus gene and P8, an 8 kDa dsRNA-binding protein encoded on a group C rotavirus gene. For example, tobacco leaf cells are infected with *Agrobacterium tumefaciens* LBA4404, transformed with plasmids containing, behind a CaMV355 promoter, either the P8 gene, the E3L gene or a mutant E3L gene, i.e., the E3L del 7C mutant, having a seven amino acid deletion from the C-terminus, resulting in a lowered affinity for binding to dsRNA of greater than 100-fold compared to wild type E3L; the E3L del 83N mutant, having an 83 amino acid deletion from the N-terminus, resulting in a protein having wild type affinity with expression occurring in the cytoplasm (wild type E3L is localized in the cytoplasm and nucleus); and the E3L G to V mutant, having the wild type glycine-164 residue replaced by a valine, resulting in a protein incapable of binding dsRNA. Comparisons between the E3L del 83N mutant-containing plants and those expressing the wild type E3L are used to quantify the effect of cytoplasmic vs. nuclear and cytoplasmic localization of the protein. Also, any undesirable effects on plant health observed with wild type E3L expression are minimized with the E3L del 83N mutant.

Transformed tobacco leaf discs were selected on kanamycin-containing medium and developing shoots were excised and placed on rooting medium. Rooted plantlets were then transplanted to artificial soil mix and grown under greenhouse conditions. Seed from self-fertilized plants was collected, surface disinfested and plated on kanamycin containing medium. Seedlings were transplanted and inoculated with TMV. Symptoms were evaluated at 5 and 14 days post-inoculation.

The tobacco plants (which are cv. Samsun nn, the susceptible genotype to TMV as demonstrated in FIG. 3) transformed to express the E3L protein, were found to be highly resistant to TMV challenge. Tobacco plants expressing the various E3L mutants had no effect on virus-reduced symptom development. As shown in FIG. 4, only plants tranformed with the E3L dsRNA-binding protein gene and challenged with TMV were able to resist viral infection as shown by the absence of coat protein when compared to controls.

Tobacco plants expressing the E3L gene appeared phenotypically different than transgenic plants in the other treatments. Specifically, the flowers are smaller but more numerous compared to untransformed and the other treatments.

A minimum of 5 independent transformants were selected for each treatment (i.e., E3L, E3L del 7C, E3L del 83N, E3L G-V, pbin 19). Ten individual plants per transformant line were inoculated with TMV at 1, 5 or 80 μg/ml inoculum. Four out of five independent transformant lines containing E3L showed local lesion development (hypersensitivity) when inoculated with TMV, regardless of the inoculum concentration, but they did not show mosaic symptoms systemically that characterize TMV susceptible reaction. The remaining lines developed characteristic symptoms of systemic TMV infection.

FIG. 5 presents transgenic tobacco (Samsun nn) plants transformed with the pBIN19 alone, E3L and E3L G-V (a nonfunctional mutant) cDNA. Sixteen days post-TMV challenge, the pBIN19 and the E3L G-V plants show the typical appearance of a virus susceptible reaction, i.e., mosaic symptoms appearing systemically throughout the plants (an enlargement of the phenotypic response is presented in FIG. 6). In contrast, the E3L transgenic plant does not show systemic symptoms. Some of the E3L transformed plants do show local lesions at the site of inoculation for virus challenge.

The expression of a gene is controlled by the promoter, the selection of which affects the expression level. A number of promoters which are active in plant and/or animal cells have been described in the literature. These include the nopaline synthase (NOS) and octopine synthase (CS) promoters (which are carried on tumor-inducing plasmids of *Agrobacterium tumefaciens*), the Cauliflower Mosaic Virus (CaMV) 19S and 35S promoters and the light-inducible promoter from the small subunit of ribulose bisphosphate carboxylase (ssRUBISCO).

In many mammalian systems, a tissue specific promoter is utilized. The tissue specific promoter causes the gene located 3' of it to be expressed predominantly, if not exclusively in the specific cells where the promoter expressed its endogenous gene. [Palmiter et al. (1986) Ann. Rev. Genet. 20:465–499].

When a tissue specific promoter is controlling the expression of a gene, that gene will be expressed in a small number of tissues or cell types rather than in substantially all tissues and cell types. Examples of tissue specific promoters include the immunoglobulin promoter [Brinster et al. (1983) Nature 306:332–336]; the elastase-I promoter [Swift et al. (1984) Cell 38:639–646]; the globin promoter [Magram et al. (1989) Mol. Cell. Biol. 9:4581–4584]; the insulin promoter [Edwards et al. (1989) Cell 58:161]; the immunoglobulin promoter [Ruscon et al. (1985) Nature 314:330–334]; the alpha actin promoter [Shani (1986) Mol. Cell. Biol. 6:2624–2631]; the alpha crystalline promoter [Overbeek et al. (1985) Proc. Natl. Acad. Sci. USA 82:7815–7819]; the prolactin promoter [Crenshaw et al. (1989) Genes and Development 3:959–972]; the proopiomelanocortin promoter [Tremblay et al. (1988) Proc. Natl. Acad. Sci. USA 85:8890–8894]; the beta thyroid stimulating hormone (BTSH) promoter [Tatsumi et al. (1989) Nippon Rinsho, 47:2213–2220]; the mouse mammary tumor virus (MMTV) promoter [Muller et al. (1988) Cell 54:105]; the albumin promoter [Palmiter et al. (1986) Ann. Rev. Genet. 20:465–499]; the Keratin promoter [Vassar et al. (1989) Proc. Natl. Acad. Sci. USA 86:8565–8569]; the osteonectin promoter [McVey et al. (1988) J. Biol. Chem. 263:11, 111–11,116]; the prostate-specific promoter [Allison et al. (1989) Mol. Cell. Biol. 9:2254–2257]; the opsin promoter [Nathans et al. (1984) Proc. Natl. Acad. Sci. USA 81:4851–4855]; the olfactory marker protein promoter [Danciger et al. (1989) Proc. Natl. Acad. Sci. USA 86:8565–8569]; the neuron-specific enolase (NSE) promoter [Forss-Pelter et al. (1986) J. Neurosci. Res. 16:141–151]; the L-7 promoter [Sutcliffe (1987) Trends in Genetics 3:73–76]; and the protamine 1 promoter [Braun et al. (1989) Genes and Development 3:793–802].

Promoters which are known or are found to cause transcription in plant cells can be used in the present invention. As described below, it is preferred that the particular promoter selected should be capable of causing sufficient expression to result in the production of an effective amount of dsRNA binding protein to render the plant substantially resistant to virus infection. The amount of dsRNA binding protein needed to induce resistance may vary with the type of plant and the infecting pathogen.

The promoters used in the DNA constructs of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. For purposes of this invention, the phrase "promoter" thus includes variations of the promoter, e.g., promoters derived by means of ligation with operator regions, random or controlled mutagenesis as well as tandem of multiple copies of enhancer elements, etc.

The use of an inducible promoter is contemplated by the invention. Usually, induction occurs as a response to a stimulating agent, e.g., light, temperature, drought, etc. It is preferred that upon viral infection, a component of the virus functions to induce expression of a dsRNA-binding protein gene.

A coding sequence used in a DNA construct of this invention may be modified, if desired, to create mutants, either by random or controlled mutagenesis, using methods known to those skilled in the art. Such mutants and variants are therefore within the scope of the present invention. Accordingly, the phrase "dsRNA-binding protein" as used herein includes native or synthetic proteins, truncated proteins and fusion proteins, capable of binding dsRNA.

The gene encoding a dsRNA-binding protein may be modified to comprise an expression enhancing modification selected from the group consisting of alteration of a translational initiation site located within the gene or in an inappropriate reading frame to a non-initiator codon, insertion of a TAA termination at the end of the dsRNA-binding protein structural gene, and utilization of plant preferred codons.

The 3' non-translated region contains a polyadenylation signal which functions to cause the addition of polyadenylate nucleotides to the 3' end of the RNA. Examples of suitable 3' regions are (1) the 3' transcribed, non-translated regions containing the polyadenylation signal of the tumor-inducing (Ti) plasmid genes of Agrobacterium, such as the nopaline synthase (NOS) gene, and (2) plant genes like the 7s soybean storage protein genes and the pea E9 small subunit of the RuBP carboxylase gene. An example of a preferred 3' region is that from the E9 gene, described in greater detail in the examples below.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAS, from suitable eukaryotic genes, or may be synthesized. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the dsRNA-binding protein, or part of the promoter sequence, or can be derived from an unrelated promoter or coding sequence as discussed above.

While in most cases the DNA which is inserted into host cells contains an individual gene which encodes a specific dsRNA-binding protein, this is not mandatory. Genes may contain, in addition to a 5' promoter region, and a 5' non-translated region, a structural coding region which encodes more than one dsRNA-binding protein, as well as a 3' non-translated region containing a functional polyadenylation signal. Those skilled in the art will recognize that one may be able to produce a fusion polypeptide containing two or more dsRNA-binding proteins from a single gene and obtain the attendant resistance to viruses and viroids. Therefore, such a modified dsRNA-binding protein gene is considered to be within the scope of the present invention in addition to the protein modifications described above.

A DNA construct of the present invention can be inserted into the genome of a plant or animal by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art.

Suitable plant transformation vectors include those derived from a Ti plasmid of Agrobacterium tumefaciens, such as those disclosed by Herrere-Estrella (1983), Bevan (1983), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells.

In one embodiment of the present invention, a cDNA sequence was prepared from a DNA segment that encodes the dsRNA-binding protein of vaccinia virus. The coding sequence was ligated to a CaMV35S promoter, and to a suitable 3' non-translated region and subsequently combined into a singular vector to form a DNA construct which comprised an individual plant gene. The vector was then inserted into cultured A. tumefaciens cells which contained a disarmed Ti plasmid.

A DNA construct prepared in accordance with the present invention is preferably introduced, via a suitable vector as described above, into cells or protoplasts derived from agriculturally important crops, e.g., dicots such as tobacco, potato, tomato, cotton, etc., or monocots such as corn, rice, etc. Regenerated plants which are tested for virus resistance are preferably exposed to one or more viruses and/or viroids at a concentration that is in a range where the rate of disease development correlates linearly with pathogen concentration in the inoculum. This linear range can be determined empirically using non-transformed plants. Methods for virus inoculation are well-known to those skilled in the art and are reviewed by Kado and Agrawal (1972 Principles and Techniques in Plant Virology). One method involves abrading a leaf surface with an aqueous suspension (typically buffered at pH 7–8) containing an abrasive material, such as carborundum or diatomaceous earth, and the virus. While inoculation in this manner is often preferred, those skilled in the art will recognize that other approaches may be used, such as simply swabbing the virus inoculum onto the leaf surface or inoculation by insect vectors, etc.

In many eukaryotic systems, a recombinant nucleic acid molecule is transported into a host cell via a vector. Any known vector, including without limitation viral vectors, retroviral vectors and plasmids, may be used.

The choice of vector to the dsRNA-binding protein gene of the present invention is operatively linked and depends directly, as is well known in the art, on the functional properties desired, e.g., replication or protein expression, and the host cell to be transformed, these being limitations inherent in the art of constructing recombinant DNA molecules. In preferred embodiments, the vector utilized includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in *Molecular Cloning: A Laboratory Manual*, Second Edition, Maniatis et al., eds., Cold Spring Harbor, N.Y. (1989) and the Lambda ZAP vectors available from Stratagene (La Jolla, Calif.). Other exemplary vectors include pCMU [Nilsson et al. (1989) Cell 58:707]. Other appropriate vectors may also be synthesized, according to known methods; for example, vectors pCMU/$K^b$ and pCMUII used in various applications herein are modifications of PCMUIV (Nilson et al., supra).

Expression vectors compatible with eukaryotic cells, preferably those compatible with vertebrate cells or plant cells can be used. Eukaryotic cell expression vectors are well known in the art and are available from several commercial sources. Typically, such vectors provide convenient restriction sites for insertion of the desired recombinant DNA molecule. Typical of such vectors are pSVO and pKSV-10 (Pharmacia), and pPVV-1/PML2d (International Biotechnology, Inc.), and pTDT1 (ATCC, NO. 31255).

Typical expression vectors capable of expressing a recombinant nucleic acid sequence in plant cells include vectors derived from the tumor-inducing (Ti) plasmid of *Agrobacterium tumefaciens* described by Rogers et al. (1987) Meth. in Enzymol. 153:253–277, and several other expression vector systems known to function in plants. See for example, Verma et al., Published PCT Application No. WO87/00551; Cocking and Davey Science (1987) 236:1259–1262.

In preferred embodiments, the eukaryotic cell expression vectors used include a selection marker that is effective in a eukaryotic cell, preferably a drug resistance selection marker. A preferred drug resistance selection marker is a gene whose expression results in neomycin resistance, i.e., the neomycin phosphotransferase (neo) gene. See for example, Southern et al. (1982) J. Mol. Appl. Genet. 1:327–341. In preferred embodiments where a recombinant nucleic acid molecule of the present invention is expressed in plant cells, a preferred drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, eds., Academic Press, Inc., San Diego, Calif. (1988).

The use of retroviral expression vectors to express recombinant nucleic acid molecules of the present invention is also contemplated. As used herein, the term "retroviral expression vector" refers to a DNA molecule that includes a promoter sequence derived from the long terminal repeat "LTR" region of a retrovirus gene and which is encapsulated in the viral protein coat capable of introducing the DNA into cells and integrating it into the cell's genome. In preferred embodiments, the expression vector is typically a retroviral expression vector that is preferably replication-incompetent in eukaryotic cells. The construction and use of retroviral vectors has been described by Sorge et al., Mol. Cell. Biol. 4:1730–1737 (1984).

The present invention is applicable to any retrovirus, including without limitation a human T-cell lymphotrophic virus, a human immunodeficiency virus, a lymphadenopathic virus, a leukemia virus, a sarcoma virus, and a virus causing a lymphotrophic disease. Such viruses include without limitation HIV, feline leukemia virus ("FeLV"), HTLV-1, HTLV-2, murine leukemia virus and avian leukemia virus. Preferably the retrovirus is HIV, HTLV-1, FeLV, or FIV.

In another preferred embodiment the expression vector is a retroviral expression vector that is replication incompetent and which already carries a marker gene such as the B-galactosidase gene. This marker gene allows cells infected by the retroviral vector to be identified by detecting the presence of the marker gene. Typically the marker gene is placed in the retroviral vector so that the non-lethal modulator gene must be coexpressed with the marker gene.

Replication incompetent retroviral expression vectors can be used to infect eukaryotic cells or tissues such as neurons and cortical progenitor cells. The infection may occur in vivo or in vitro. Retroviral vectors carrying a β-galactosidase marker gene have been used to infect neurons by Luskin et al., Neuron, 1:635–647 (1988).

Also contemplated by the present invention are tissues containing a recombinant nucleic acid molecule. Tissues containing a recombinant nucleic acid molecule of the present invention may be prepared by introducing a recombinant nucleic acid molecule into a tissue, such as bone marrow, brain and liver, using known transformation techniques. These transformation techniques include transfection and infection by retroviruses carrying either a marker gene or a drug resistance gene. See for example, Current Protocols in Molecular Biology, Ausubel et al., eds., John Wiley and Sons, New York (1987) and Friedmann, T. (1989) Science 244:1275–1281. A tissue containing a recombinant nucleic acid molecule of the present invention may then be reintroduced into an animal using reconstitution techniques. See for example, Dick et al. (1985) Cell 42:71.

A tissue containing a recombinant nucleic acid molecule of the present invention may also be prepared by introducing a recombinant DNA molecule of the present invention into the germ line of a mammal. After introduction into the germ line, the recombinant DNA molecule is present in all the tissues of that mammal. See for example, Palmiter et al. (1986) Ann. Rev. Genet. 20:465–499.

Isolation of tissues from an animal whose tissues contain the recombinant nucleic acid molecule is accomplished using standard techniques. For example, the liver, lungs, spleen, or bone marrow can be removed using standard surgical techniques.

A tissue containing a recombinant DNA molecule of the present invention may also be produced by directly introducing a vector containing the recombinant DNA molecule into the animal. Direct vector delivery in vivo may be accomplished by transducing the desired cells and tissues with viral vectors or other physical gene transfer vehicles in vivo. Other physical agents including naked plasmids, cloned genes encapsulated in targetable liposomes or in erythrocyte ghosts have been used to introduce genes, proteins, toxins and other agents directly into whole animals. See for example, the liposome-mediated gene delivery in vivo and expression of preproinsulin genes in recipient rats described by Nikolau et al. (1983) Proc. Natl. Acad. Sci. USA 80:1068 and Soriano et al. (1983) Proc. Natl. Acad. Sci. USA 80:7128. Direct injection of naked calcium phosphate-precipitated plasmid into rat liver and rat spleen or a protein-coated plasmid into the portal vein has resulted in gene expression of the foreign gene in the rat livers. See for example, Kaneda et al. (1989) Science 243:375.

The present invention also contemplates a mammal containing a recombinant nucleic acid molecule of the present invention. Mammals containing recombinant nucleic acid molecules of the present invention may be prepared using the standard transgenic technology described in Hogan et al (1987) Manipulatina the Mouse Embryo: A Laboratory Manual, Cold Spring Harbor, N.Y.; Palmiter et al. (1986) Ann. Rev. Genet. 20:465–499. Production of transgenic animals is also possible using the homologous recombination transgenic systems described by Capecchi (1989) Science 244:288–292.

Preferred embodiments of the present invention contemplate a method of altering a complex biochemical pathway within a cell of a transgenic mammal by producing a transgenic mammal having at least one cell containing and expressing a recombinant nucleic acid molecule of the present invention. The recombinant nucleic acid molecule containing transgenic mammal is maintained for a time period sufficient for the dsRNA-binding protein gene present in the recombinant nucleic acid molecule to be expressed in the cell and thereby alter a complex biochemical pathway within the cell of the transgenic mammal.

Transgenic mammals having at least one cell containing a recombinant nucleic acid molecule of the present invention can be produced using methods well known in the art. See for example, Wagner et al. U.S. Pat. No. 4,873,191 (Oct. 10, 1989); Hogan et al., Manipulating the Mouse Embryo: A Laboratory Manual, Cold Springs Harbor, N.Y. (1987); Capecchi (1989) Science 244:288–292; and Luskin et al. (1988) Neuron 1:635–647.

EXAMPLE 1

Gene Constructions Encoding dsRNA-binding Proteins

E3L and P8 are dsRNA binding proteins synthesized by vaccinia virus and rotavirus, respectively. E3L is an Mr 25,000 protein and P8 is an Mr 8,000 protein. The E3L and P8 genes have been cloned and characterized. The C-terminal segments of the E3L protein and the P8 protein contain a consensus motif involved in dsRNA binding.

The construction of vectors containing the E3L gene is described in Chang et al. (1992, Proc. Natl. Acad. Sci. 89:4825–4829. Briefly, the E3L gene of vaccinia virus (WR strain) was amplified by PCR from plasmid containing the HindIII E fragment of vaccinia virus (WR strain) [Moss et al. (1981) Virology 112:306–317]. Two primers: 5'-TCGCGAATTCATGGTCTAAGATCTATATT-3' (SEQ ID NO: 2) and 5'-AGGCCTGCAGTCAGAATCTAATGATTAC-3' (SEQ ID NO: 3), which correspond to 5' and 3' sequences of the E3L ORF were used to amplify the gene. The amplified E3L gene was cloned into the EcoRI and Pst I sites of PBS-KSII+ (Stratagene) vector. The pBluescript plasmid containing the E3L gene was designated pBS-E31.

pMt2/Va-vector [Kaufman et al. (1989) Mol. Cell. Bio. 9:946–958] was modified as follows: pMT2/Va- was digested with EcoRI and blunt ended with Klenow fragment of DNA polymerase I. Calf intestinal alkaline phosphatase was used to remove the 5'-terminal phosphate group of the modified pMT2/Va- vector. The E3L gene was removed from pBS-E3L by EcoRI and BamHI digestion. The E3L gene was then blunt ended by DNA polymerase I Klenow fragment-catalyzed filling and subcloned into the modified pMT2/Va- vector. The pMT2/Va- vector containing the correct orientation of E3L gene was designated pMT-3EL

EXAMPLE 2

Gene Constructs of Deletion Mutants of E3L.
(a) Construction of Carboxyl Terminus Deletion Mutants of E3L.

The E3L C-terminus deletion mutants were constructed by polymerase chain reaction (PCR) using pBS-E3L [Chang et al., (1992) Proc. Natl. Acad. Sci. 89:4825–4829] as the template. Briefly, a 5'-sense primer, 5' AGGCCTGCAGAT-GTCTAAGATCTATATT 3' (SEQ ID NO: 4), which corresponds to nucleotides (nt) 1–18, was used to construct all C-terminus deletion mutants. The following 3' anti-sense primers were used to PCR-amplify E3L mutants: 5' TCGC-GAATTCTCAGAATCTAATGATGAC 3' (SEQ ID NO: 5), which corresponds to nt 556-573 of E3L gene, was used to amplify E3L/1-7 (also called E3L del 7C) (full length, AA 1-190); 5' TCGCGAATTCCTAAAGAAGTTTATCTAC 3' (SEQ ID NO: 6), which corresponds to nt 535-549, followed by a translation terminator, was used to amplify E3L/2-2

(AA 1-183); 5' TCGCGAATTCCTATCCATCTGCCTTATC 3' (SEQ ID NO: 7), which corresponds to nt 478-492, followed by a translation terminator, was used to amplify E3L/3-5 (AA 1-164); 5' TCGCGAATTCCTATTCAATAC-GAAAAGA 3' (SEQ ID NO: 8), which corresponds to nt 400-414, followed by a translation terminator, was used to amplify E3L/4-5 (AA 1-138). The full-length E3L DNA (E3L/1-7) and the E3L mutants containing C-terminus deletions (E3L/2-2, E3L/3-5, E3L/4-5) were cloned into the EcoRI and Pst sites of pBS-KSII+ (Stratagene) and dideoxy sequencing was performed to confirm the sequence of the inserts. The pBluescript plasmids containing E3L/1-7, E3L/2-2, E3L/3-5, AND E3L/4-5 were designated pBS-E3L/1-7, pBS-E3L/2-2, pBS-E3L/3-5, AND pBS-E3L/4-5, respectively. The full-length and mutant E3L DNAs were removed from the pBluescript plasmids and subcloned into the EcoRI and PstI sites of pMT2/Va- vector [Kaufman et al. (1989) Mol. Cell. Biol. 9:945–958]. Cloning into these sites of pMT2/Va-interrupts the expression of the plasmid encoded dihydrofolate reductase gene.

(b) Construction of the Amino Terminus Deletion Mutant of E3L.

pGEM3-5T vector [Patel and Sen, (1992) J. Biol. Chem. 267:7671–7676] was modified as follows: pGEM3-5T was digested with SmaI and SalI. Calf intestinal alkaline phosphatase was used to remove the 5'-terminal phosphate group of the modified pGEM3-5T vector. pBS-E3L/1-7 DNA was digested with AatII and blunt-ended with T4 DNA polymerase. The DNA was then digested with SalI. The AatII (blunt-ended)-SalI fragment of E3L (84–190) was subcloned into the modified pGEM3-5T vector. The pGEM3-5T vector containing the E3L gene with 83 amino acids deleted from the N-terminus is designated pGEM-5T-E3L/AatII. The E3L/AatII fragment was removed from pGEM-5T-E3L/AatII by EcoRI digestion and subcloned into the EcoRI site of pMT2/Va- vector. The pMT2/Va- vector containing the correct orientation of E3L/AatII DNA was designated pMT-E3L/AatII.

(c) Construction of Point Mutation Mutants of E3L.

The E3L point mutants were constructed using a PCR-based method of site-directed mutagenesis [Sarkar and Sommer (1990) BioTechniques 8:404–407]. Three primers were used and two PCRs were performed to generate site-specific sequence changes for each point mutation. Briefly, in the first round of PCR, primer 5' TCGCGAATTCTCA-GAATCTAATGATGAC 3' (SEQ ID NO: 5), which corresponds to nt 556–573 and 5' GGCAGATGHAAAATCTA 3' (SEQ ID NO: 9), which corresponds to nt 483–499 (H could be either a C, T, or A instead of a G, as in wild type E3L), were used in the presence of template pBS-E3L to amplify the segment containing nt 483 to nt 573 (E3L/483–573). The amplified E3L/483–573 was purified by agarose gel electrophoresis and used as a "megaprimer" in the second round of PCR in the presence of primer 5' AGGCCTGCAGAT-GTCTAAGATCTATATT 3' (SEQ ID NO: 4), which corresponds to nt 1-18 and template pBS-E3L. The amplified E3L DNA bearing sequence changes at nt 491 was cloned into the EcoRI and PstI sites of pBS-KS II+vector. Twelve colonies were isolated and plasmid DNA was sequenced. Two clones, pBS-E3L/164-G-V (which has a T at nt 491, resulting in an amino acid change from Gly to Val at amino acid 164) and pBS-E3L/164-G-A (which has a C at nt 491, resulting in an amino acid change to Ala) were used for further analysis. E3L mutants which contain mutations at amino acid 167 were generated in a similar manner, using 5' AAAATC-TABACGAGATGC 3' (SEQ ID NO: 10), which corresponds to nt 492-509 (B could be either a T, C or G instead of an A, as in wild type E3L), as the mutagenic primer. Two clones, pBS-E3L/167-K-R (which has a G at nt 500, resulting in an amino acid change from Lys to Arg at amino acid 167) and pBS-E3L/167-K-T (which has a C at nt 500, resulting in an amino acid change to Thr) were used for further analysis. E3L mutants which contain mutations at AA 174 were generated using 5' AAATAATGDAGCTAAAT 3' (SEQ ID NO: 11), which corresponds to nt 513-529 (D could be either a G, A, or T instead of a C, as in wild type E3L), as the mutagenic primer. Two clones, pBS-E3L/174-A-G (which has a G at nt 521, resulting in an amino acid change from Ala to Gly at AA 174) and pBS-E3L/174-A-V (which has a T at nt 521, resulting in an amino acid change from Ala to Val), were used for further analysis. The E3L/164-G-V, E3L/164-G-A, E3L/174-A-G, and E3L/174-A-V DNAs were removed from the pBluescript plasmids and subcloned into the EcoRI and PstI sites for pMT2/Va-vector.

EXAMPLE 3

Transcription and Translation of Genes Encoding dsRNA-binding Proteins (a) In vitro system.

Five micrograms of pBluescript or pGEM-5T plasmids containing wild type or mutant E3L DNA were linearized with HindIII, and T7 RNA polymerase (Promega) was used according to the manufacturer's specifications to transcribe RNA. After completion of the transcription reaction, samples were treated with DNase and extracted with phenol chloroform and chloroform. RNA was then precipitated from the samples with ethanol and resuspended in 20 $\mu$l of diethylpyrocarbonate-treated water. Aliquots of RNA (10 $\mu$l) were used in in vitro translation reactions (Promega). The translation reaction mixture contained 35 $\mu$l of nuclease-treated rabbit reticulocyte lysate, 20 units of RNasin, 20 $\mu$M amino acid mixture minus methionine, and 50 $\mu$Ci of [$^{35}$S] methionine (1186 Ci/mmol; 1 Ci–37 GBq). The reactions were carried out at 30° for 1.5 hr. After completion of the reaction, 15 $\mu$l of the mixture was bound to poly(rI)·poly (rC)-agarose or precipitated with antibodies to p25 (E3L).

(b) In Vivo System: Transfection of COS Cells.

This method is essentially that described in Langland et al. (1994) J. Virology 68:3821–3829. Briefly, two micrograms of pMT2/Va- plasmid containing the full-length or deletion-mutant E3L DNA were transfected into COS cells by the DEAE-dextran method with chloroquine treatment [Giantini and Shatkin (1989) Meth. Mol. Biol. 10:23–30]. To radiolabel newly synthesized proteins, medium was aspirated off the COS cells and 1.5 ml of Dulbecco's minimal essential media (DMEM) without methionine was added. After 30 min. of incubation at 37°, the medium was removed and 150 $\mu$l of DMEM lacking nonradioactive methionine and containing 1% dialyzed fetal calf serum and 50 $\mu$Ci of [$^{35}$S]methionine per milliliter was added. The cells were incubated for 30 min. at 37° and cytoplasmic extracts were prepared. For preparing cytoplasmic extracts, monolayers were washed with cold isotonic buffer (35 mM Tris-HCl, pH 6.8, 146 mM NaCl, 11 mM glucose) and scraped into the buffer. Cells were then pelleted by centrifugation at 1000 g and resuspended in Nonidet P-40 lysis buffer [20 mM HEPES, pH 7.5, 120 mM KCl, 5 mM MgCl$_2$, 1 mM dithiothreitol (DTT), 10% (vol/vol) glycerol, 0.5% Nonidet P-40; 100 $\mu$l of Nonidet P-40 lysis buffer per 10$^7$ cells]. The resuspended cells were sonicated twice for 10 sec each (Bransonic 52). Nuclei and cell debris were removed by centrifugation at 10,000 g for 10 min at 4° C. The cytoplasmic extracts were collected and stored at −80° C.

Fifteen microliters of extract was used for each immune precipitation. Relative amounts of the full-length and mutant E3L proteins expressed in COS cells were measured by scanning densitometry and corrected for the number of methionine residues present in the proteins to ensure that equal moles of E3L proteins were used in poly(rI)·poly(rC)-agarose binding and kinase reactions.

(c) Poly(rI)·Poly(rC)-Agarose and Reovirus dsRNA-Agarose Binding.

Poly(rI)·poly(rC)-agarose or reovirus dsRNA-agarose [Langland et al. (1992) J. Biol. Chem. 267:10729–10736] was washed three times in buffer A (150 mM KCl, 20 mM HEPES, pH 7.5, 10% glycerol, 5 mM MgOAc, 1 mM benzamidine). [$^{35}$S]methionine-labeled in vitro translation mixtures or cytoplasmic extracts from [$^{35}$S]methionine-labeled COS cells were added to the washed poly(rI)·poly(rC)-agarose and incubated at 4° C. with occasional mixing for one hour. In the experiment to test the effect of competing soluble nucleic acids, the indicated concentration of nucleic acid was added to the cell extract prior to mixing extract and agarose. The agarose was then washed three times in buffer A. dsRNA-binding proteins were eluted from the agarose by adding an equal volume of 2× SDS/PAGE sample buffer and boiling for 3 min. Proteins were separated by SDS/PAGE and visualized by autoradiography.

(d) Radioimmune Precipitation.

Ten microliters of normal rabbit serum or p25-specific antiserum [Watson et al. (1991) Virology 185:206–216] were incubated with 15 μl of [$^{35}$S]methionine-labeled in vitro translation mixture or extract from [$^{35}$S]methionine-labeled COS cells for two hours on ice. One hundred microliters of washed, fixed, Staphylococcus aureus cells (Boehringer-Mannheim, Indianapolis, Ind.) were then added and incubation was continued on ice for one hour. The S. aureus cells were collected by centrifugation and washed three times in RIPA buffer (10 mM Tris-HCl, pH 7.4, 1% deoxycholate, 1% Nonidet P-40, 0.15 M NaCl, 1 mM benzamidine, 1 mM DTT) and once in 0.1 M Tris-HCl (pH 7.4). Bound proteins were eluted by boiling with 2× SDS/PAGE sample buffer for three minutes. Proteins were resolved by SDS/PAGE and visualized by autoradiography.

(e) PI/eIF-2 Kinase Inhibitory Activity.

Extracts of COS cells which contained equimolar amounts of the full-length or mutant E3L proteins were added to the kinase reaction mixture [20 mM HEPES, pH 7.5, 120 mM KCl, 5 mM MgOAc, 1 mM DTT, 100 μM [γ-$^{32}$P]ATP (1 Ci/mmol)] containing extract prepared from interferon-treated, uninfected mouse L cells (5×10$^5$ cells) as a source of kinase and the indicated concentrations of reovirus dsRNA in a final volume of 20 μl. The kinase reaction was carried out at 30° C. for 15 min and was stopped by addition of an equal volume of 2× SDS/PAGE sample buffer. The reaction samples were boiled for three minutes and proteins were resolved by SDS/PAGE and visualized by autoradiography.

(f) Relative dsRNA Binding Affinity.

Increasing concentration of soluble poly(rI)·poly(rC) (0 to 100 μg/ml) were incubated for one hour on ice with extracts of transfected COS cells which contained equimolar amounts of [$^{35}$S]methionine-labeled E3l/1-7, E3L/2-2, or E3L/AatII proteins. Buffer A washed poly(rI)·poly(rC)-agarose was then added to the mixture and incubated on ice for one hour with occasional mixing. The agarose was then washed three times in buffer A. Proteins were eluted from the agarose by adding an equal volume of 2× SDA/PAGE sample buffer and boiling for three minutes. Proteins were separated by SDS/PAGE and visualized by autoradiography.

The relative amount of E3L proteins bound to poly(rI)·poly(rC)-agarose were determined by scanning densitometry of the autoradiogram. The maximal binding of E3L proteins to poly(rI)·poly(rC)-agarose was in the presence of no soluble poly(rI)·poly(rC) and was given the arbitrary value of 100%. The relative amount of E3L proteins bound to soluble poly(rI)·poly(rC) was obtained by subtracting the value of E3L proteins bound to poly(rI)·poly(rC)-agarose from 100%.

EXAMPLE 4

Assay for Ihibition by dsRNA-binding Poteins on PI/eIF-2 Knase Ativity

The assay method is essentially as described in Chang et al. (1992) Proc. Natl. Acad. Sci. 89:4825–4829. Briefly, extracts prepared from COS cells transfected with pMT-E3L or pMT2/Va- plasmid were added to the kinase reaction mixture [20 mM HEPES, pH 7.5/120 mM KCl/5 mM MgOAc/1 mM DTT/100 μM [γ-$^{32}$P]ATP (1 Ci/mmol)] containing extract prepared from interferon-treated, uninfected L cells (5×10$^5$ cells) as a source of kinase and the indicated concentrations of reovirus dsRNA in a final volume of 25 μl. The kinase reaction was carried out at 30° C. for 15 minutes and was stopped by addition of an equal volume of 2× SDS/PAGE sample buffer. The reaction samples were boiled for three minutes and proteins were resolved by SDS/PAGE and visualized by autoradiography.

Alternatively, dsRNA-binding proteins were assayed for PKR kinase inhibitory activity, as described in Langland et al. (1994) J. Virology 68:3821–3829.

EXAMPLE 5

Transformation and Regeneration of Tobacco (a) Plant Growth Media.

Shoot regeneration medium (3C5ZR) contained the salts of Murashige and Skoog (MS) (1962) Physiol. Plant. 15:473–497, obtained from Flow Laboratories or Gibco. This was supplemented with 1 mg/l Thiamine HCl, 0.5 mg/l nicotinic acid and 0.5 mg/l pyridoxine HCl (R3 vitamins); 3% sucrose, 5 μM zeatin riboside and 3 μM indole-3-acetic acid aspartic acid, pH 5.9. The medium was solidified with 0.8% Difco agar. Transformed shoots were selected on shoot regeneration medium containing 100 μg/ml kanamycin and 500 μg/ml carbenicillin. Explanted shoots were rooted in MS medium containing R3 vitamins and sucrose with 100 μg/ml kanamycin and 200 μg/ml carbenicillin.

(b) Bacterial Strains.

Agrobacterium tumefaciens LBA 4404 containing the disarmed kanamycin resistance vector pBin6 [Bevan (1984) Nucl. Acids Res. 12:8711–8721] was used for all infections. The strain was grown in 10 mls of LB at 30° C. containing 50 μg/ml kanamycin for 24 hours before us, at which time it was centrifuged and resuspended in 20 mls of MS medium before plant transformation.

(c) Plant Material.

Nicotiana tabacum (cv. Samsun nn), the susceptible genotype to tobacco mosaic virus, TMV, was used for transformation studies.

(d) Transformation Vector Construction.

The E3L and E3L mutant genes were subcloned as pMT-E3L, pMT-E3L/1-7, pMT-E3L/Aatl1 AND pMT-E3L/164-G-V, respectively, into pBin 19 [Bevan, M. (1984) Nuc. Acids Res. 12:8711] using the procedure essentially as described in Miki et al. (1993) Methods in Plant Mol. Biol. and BioTechnology, CRC Press, 67–80.

(e) Transformation and Regeneration.

Nicotiana tabacum (cv. Samsun nn), the genotype susceptible to tobacco mosaic virus (TMV), was transformed with E3L and E3L mutant genes using standard procedures as outlined for example in Miki et al. (1993) Meth. in Plant Mol. Biol. and BioTechnology, CRC Press, 67–80. Prior to transformations, the tobacco plants were screened for TMV reaction by transplanting random seedlings from a tobacco seed lot. Five random seedlings were mechanically inoculated with TMV [50 µg of inoculum (at a concentration of 10 µg/ml) per leaf on each of two leaves]. All plants developed symptoms characteristic of systemic TMV infection. Uninfected leaves from the remaining plants were excised and used for transformation by the leaf disk method.

Agrobacterium tumefaciens LBA4404 were transformed [Miki et al. (1993) supra] with the plasmids containing the target genes, i.e., E3L, E3L del 7C, E3L del 83N, E3L G-V AND bin 19 behind a single CaMV 35S promoter. Transformed Agrobacterium colonies were selected on selective medium and the presence of the target genes was confirmed by digesting a mini-preparation and visualization on agarose gels with appropriate controls. Briefly, tobacco leaves were surface sterilized and leaf discs (25 per treatment) were excised. The discs were incubated with the appropriate Agrobacteria according to standard procedures (Miki et al. 1993, supra). Transformed discs were selected on kanamycin-containing medium and developing shoots were excised and placed on rooting medium. Rooted plantlets were then transplanted to artificial soil mix and grown under greenhouse conditions (25° C., 18h daylength). Plants were fertilized weekly and sprayed with insecticide when needed. Seed from self-fertilized plants was collected, surface disinfected and plated on kanamycin-containing medium. Seedlings were transplanted and inoculated with TMV (50 μl inoculum on each of two leaves with 1, 5 or 80 μg/ml concentration levels). Symptoms were evaluated at 5 and 14 days post-inoculation.

Tobacco plants expressing the E3L gene appear phenotypically different than transgenic plants in the other treatments. Specifically, the flowers are smaller, but more numerous compared to untransformed and the other treatments. No other differences were noted.

A minimum of five independent transformants were selected for each treatment (i.e., E3L, E3L del 83N, E3L del 7C, E3L G-V, pbin 19). Ten individual plants per transformant line were inoculated with TMV at 1, 5 or 80 μg/ml inoculum. Four out of five independent transformant lines containing E3L showed local lesion development (hypersensitivity) when inoculated with TMV, regardless of the inoculum concentration. The remaining lines developed symptoms characteristic of systemic TMV infection. These assays were repeated with the same results.

EXAMPLE 6

Transformation and Regeneration of Potato (a) Plant Material.

Virus-free tubers of *S. tuberosum var*. Pentland Dell were obtained from SCRI; Desiree, Maris Piper, Maris Bard and Golden Wonder were from the PBI. Only fresh tubers (less than six months old and stored at 4–6° C.) were used for transformation experiments.

Plant growth media are described in Sheerman et al. (1988), Plant Cell Reports 7:13–16.

(b) Bacterial Strains.

*Agrobacterium tumefaciens* LBA 4404 containing the disarmed kanamycin resistance vector pBin6 [Bevan (1984) Nucl. Acids Res. 12:8711–8721] was used for all infections. The strain was grown in 10 mls of LB at 30° C. containing 50 μg/ml kanamycin for 24 hours before use, at which time it was centrifuged and resuspended in 20 mls of MS medium before plant transformation.

(c) Transformation Vector Construction.

The E3L and E3L mutant genes were subcloned as pMT-E3L, pMT-E3L/1-7, pMT-E3L/AatII and pMT-E3L/164-G-V, respectively, into pBin 19 [Bevan (1984) supra] using the procedure essentially as described in Miki et al. (1993) supra.

(d) Co-cultivation of *A. tumefaciens* and Potato Tissues.

Tubers were peeled, washed briefly in distilled water, and surface-sterilized for 15 minutes in a 10% solution of sodium hypochlorite containing a few drops of 'Tween 20'. They were then washed six times in sterile distilled water and finally immersed in liquid MS medium.

Samples were taken using a sterile 1 cm diameter cork borer, and columnar sections were sliced into thin discs (approximately 1–2 mm thick) using a scalpel. The tuber discs were floated in 20 mls of MS medium containing Agrobacterium and thoroughly wetted by gently shaking the petri dish. After 20 minutes the tuber discs were transferred to tobacco feeder plates [Horsch et al. (1985) Science 277:1229–1231] containing 3C5ZR medium. After 48 hours, infected discs were replated on identical medium lacking the feeder layer containing carbenicillin (500 μg/ml) for Agrobacterium elimination, and kanamycin (100 μg/ml) for selection of transformed tissue. The plates were sealed with parafilm and incubated at 25° C. under a 16-hour daylength. Tuber discs were subcultured onto fresh regeneration medium at three weekly intervals, lowering the carbenicillin concentration from 500 μg/ml to 200 μg/ml after four weeks in culture. Developing shoots were removed and replated in large test tubes containing MS salts and R3 vitamins plus carbenicillin (200 $\mu g/ml^{-1}$) and kanamycin (100 $\mu g/ml^{-1}$) for root induction. ps Nopaline Assays Nopaline was extracted from approximately one-month-old shoots and analyzed according to Otten and Schilperoort (1978) Biochim. Biophys. Acta 527:494–500.

DNA Analysis

DNA was extracted from stem and leaf tissue of axenic plants as described [Bevan (1984) Nuc. Acids Res. 12:8711–8721], digested with BamHI and Southern blotted [Maniatis et al. (1982) Molecular Cloning: A laboratory manual. Cold Spring Harbor Press, New York]. The blot was probed with an oligomer primed DNA fragment containing part of the nopaline synthase gene.

EXAMPLE 7

Transformation and Regeneration of Tomato

Methods and procedures used for the transformation and regeneration of tomato were carried out essentially as described in Nelson et al. (1988) Biotechnology 6:403–409.

EXAMPLE 8

Detection of Viral Replication

Virus replication in mammalian cells is measured or estimated using standard methodology based upon, for example, the plaque assay [Dulbecco (1952) Proc. Natl. Acad. Sci. 38:747], Western blotting for detection of viral antigens [Chu et al., "Assessment of a method for immunochemical detection of antigens on nitrocellulose membranes," J. Histochem. Cytochem. (1989) 37:257–263].

Methods used to detect virus/viroid replication in plants cells are carried out, for example, as described for Western blotting for detection of viral antigens [Langland et al. (1995) Plant Physiol. 108:1] and in vivo labeling of proteins [Chang et al. (1993) Virology 194:537–547]. A coat protein assay may be carried out in transgenic plants according to Nelson et al. (1988) Biotechnology 6:403–409.

The presence of viroids may be detected using a viroid cDNA probe. Owens et al. (1986) Plant Mol. Biology 6:179–192.

EXAMPLE 9

Assays for Identifying a dsRNA-Binding Protein

A dsRNA-binding protein may be isolated and purified by binding to dsRNA-agarose as described in Langland et al. (1995) Protein Expression and Purification 6:25–32.

Alternatively, a dsRNA-binding protein may be immunoprecipitated from tissue extracts using antiserum to a synthetic peptide corresponding to the consensus sequence dsRNA-binding domain [Chang et al. (1993) Virology 194:537–547].

Also, a gene encoding a dsRNA-binding protein may be identified by screening cDNA expression libraries to cloned dsRNA-binding protein cDNAs [Langland et al. (1994) J. Virology 68:3821–3829].

In addition, dsRNA-binding proteins are usually recognized by the amino acid sequence of the dsRNA-binding domain which may comprise the consensus sequence characteristic of dsRNA-binding domains [Chang et al. (1993) supra].

EXAMPLE 10

Gene Therapy With a dsRNA-binding Protein Gene

Patients infected with a virus having a dsRNA-like structure can be provided with a gene therapy destined to improve or decrease symptoms associated with the viral infection and/or to provide broad resistance against viruses having a dsRNA-like structure. In essence, the gene therapy consists of introducing into a patient a gene encoding the E3L protein, which binds to dsRNA-like structures with high affinity, such that E3L protein is expressed in amounts sufficient to complex the available cytoplasmic dsRNA-like structures. Phenotypic symptoms characterizing the viral infection are reduced as a result of the gene therapy and the patient, stably transformed with the E3L protein gene, is provided with a means to continually complex any intracellular dsRNA-like structure that becomes available.

The present invention provides a dsRNA-binding protein gene, i.e., an E3L gene, in a vector capable of being transformed into a plant cell and into a mammalian cell. Transient expression of E3L in mammalian cell cultures has also been described in Giantini et al. (1989) J. Virology 63:2415–2421.

At present, only biological transfer via viral vectors is efficient enough to be used in gene transfer procedures. The viral gene transfer system that is most researched and advanced is based on disabled murine retroviruses [Anderson (1984) Science 226:401–409]. Methods for transferring a genetically-engineered nucleic acid molecule for human gene therapy are known in the art [Anderson et al. (1995) Gene Therapy, U.S. Pat. No. 5,399,346; Greatbatch et al. (1994) "Method of conferring resistance to retroviral infection," U.S. Pat. No. 5,324,643; Srivastava (1993) "Safe vector for gene therapy," U.S. Pat. No. 5,252,479; Burton et al. (1995) "Cholera toxin gene regulated by tissue-specific promoters"; Mullen et al. (1994) "Cytosine deaminase negative selection system for gene transfer techniques and therapies," U.S. Pat. No. 5,358,666; Tolstoshev (1993) "Current Status and Future Directions in Human Gene Therapy. Advances in Genome Biology 2:389–415; Cornetta et al. (1991) Human Gene therapy 2:5–14; Smith et al. (1993) Nature Genetics 5:397–402; and Perkinson et al. (1993) J. Tissue Culture Methods 15:72–81].

A particular embodiment of the present invention provides gene therapy for AIDS (Acquired Immune Deficiency Syndrome). For this purpose, the invention contemplates the use of retroviral mediated transfer. As described in Morgan et al. (1991*, Advances in Molecular Biology and Targeted Treatment for AIDS*, Kumar, ed., Plenum Press, New York, pp. 301–308), retroviral mediated gene transfer is dependent on a two component system, the packaging cell and the viral vector. A packaging cell is a cell which contains a retroviral genome from which the signals that are responsible for the encapsidation of the viral genome into virus particles have been removed. Thus, the viral genome in the packaging cell line produces all the proteins necessary for virus replication and assembly, but cannot create an infectious particle due to the lack of a transferable viral genome. Into the packaging cell line can be introduced a genetically engineered retroviral genome known as a retroviral vector. The retroviral vector is the complement to the packaging cell genome in that all the normal viral protein coding sequences have been removed, but the encapsidation and replication signals have been retained. A gene encoding dsRNA-binding protein can be inserted into the retroviral vector by molecular cloning.

The virus particle assembled by the producer cell line (a producer cell line is defined as a packaging cell line containing a retroviral vector) can then be used to transfer the retroviral vector sequence to another cell. Upon addition of the retroviral vector to a culture of cells the vector sequence is integrated into the host genome. Because of the defective nature of the retroviral vector, this transfer procedure is termed transduction to contrast it with infection, which is reserved for replication competent viruses. Once integrated, the internal sequences of the retroviral vector can be expressed leading to the production of a new protein in the transduced cell.

The most promising feature of retroviral vectors as anti-HIV agents is their ability to deliver a gene or gene product precisely where you want it, at or in the cell. This can have enormous advantages for biological compounds which may only function in the intracellular environment or for compounds which need to be present in a high local concentration. Because retroviral vectors are stably integrated into the host cell chromosomes, it can be expected that they will express a given protein on a continuous basis. In retroviral-mediated gene transfer, the use of ex vivo transduction protocols can permit the engineering of specific cell populations. Thus, it may be possible to protect CD4+ T-cells from HIV infection by first isolating the cells from the bulk lymphocyte population, engineering them, and then returning them to the body. It may also be possible to engineer cells in the macrophase lineage, and then use the natural properties of these cells to transfer anti-HIV agents to the brain (since they are suspected of delivering the HIV virus itself). All of these factors combine to make retroviral vectors a potentially promising anti-HIV system.

A direct attack on the HIV virus is possible at any stage of its intracellular life cycle. The strategy invoked by the present invention is to inhibit HIV by inhibition of dsRNA-like structures that are critical to a vital viral process, e.g., replication.

The trans-acting response region (TAR) RNA sequence of the HIV assumes a dsRNA-like structure, i.e., a stable, highly-paired, stem loop structure. The TAR region binds to a HIV tat protein and activates transcription and translation. Thus, the dsRNA-like structure, i.e., the TAR region, is necessary for viral replication.

Figure 7:
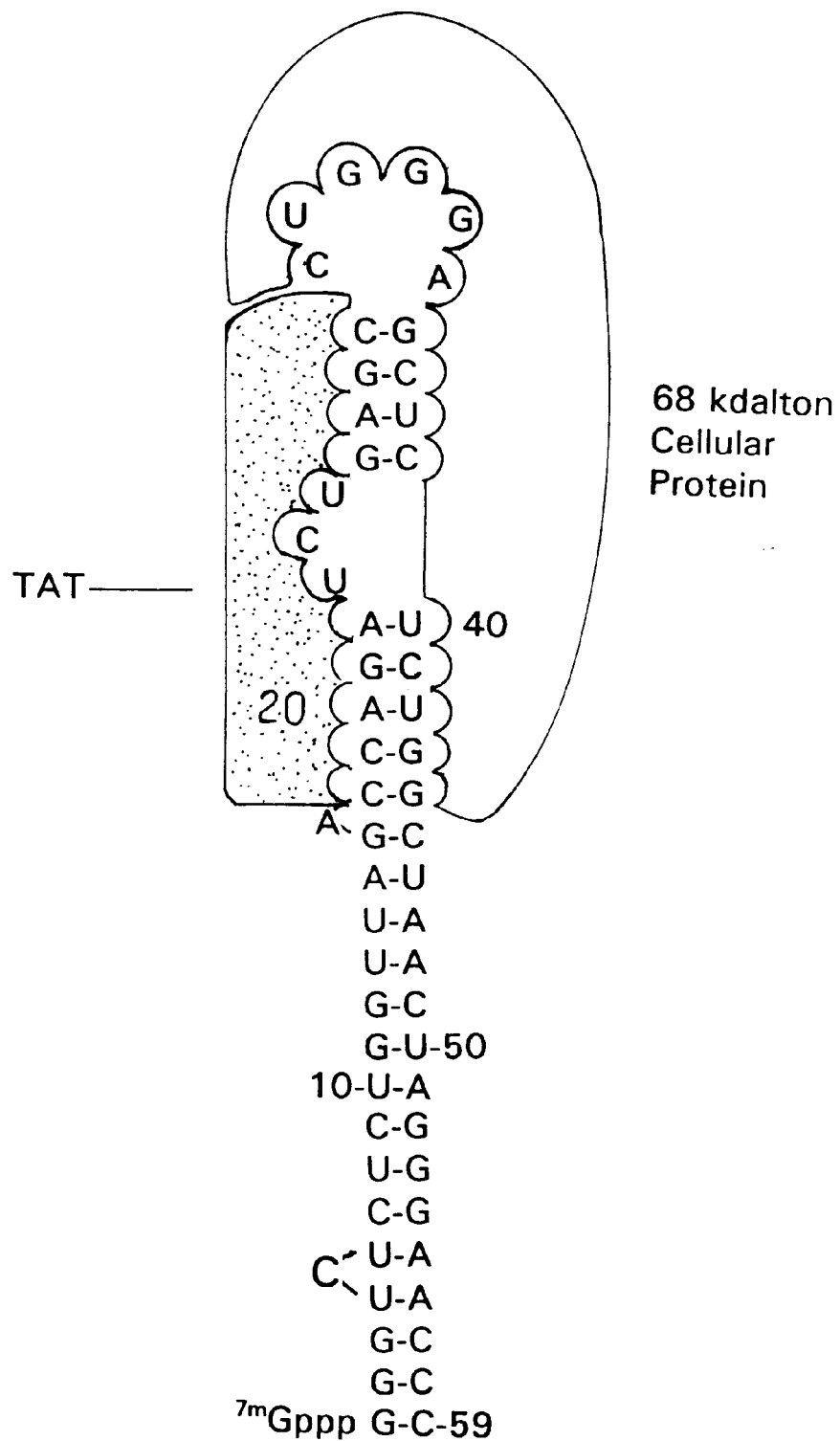
Figure 8:
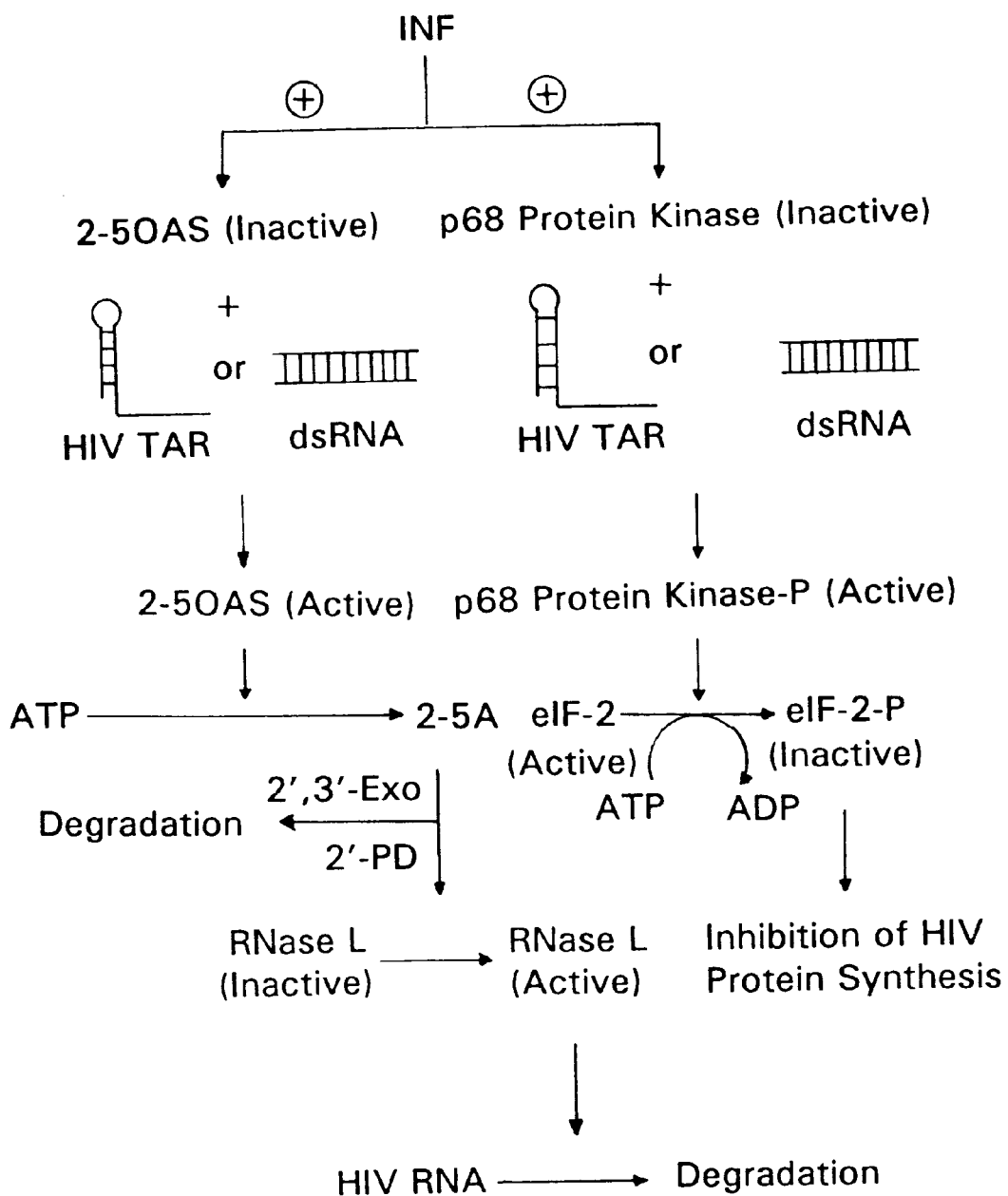

FIG. 7 illustrates schematically the apparent similarities between TAR and dsRNA in mediating the activation of enzymes induced in the interferon cycle. E3L binds to a dsRNA-like structure and prevents activation of the 2'5'-oligoadenylate synthetase (250AS) and the dsRNA-dependent RNA protein kinase (PKR) enzymes. The TAR-binding protein and the E3L protein both comprise a dsRNA-binding domain having a characteristic amino acid consensus sequence indicating that E3L binds to the TAR region. The binding of E3L to the TAR region has an "anti-tat" effect, preventing activating of transcription and translation.

The ability to continually express a protein, E3L, capable of binding to a dsRNA-like structure at the site of HIV infection, constitutes a means for inhibiting HIV replication in host cells. By complexing dsRNA-like structures that are required for replication with E3L protein that is being continually expressed in the transformed cells, not only is the initial infection therapeutically treated but, in addition, dsRNA-binding protein is continually expressed as a means for preventing renewed appearance of the phenotypic symptoms of infections.

```
                              SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
          (A) LENGTH: 24 amino acids
          (B) TYPE: amino acid
          (C) STRANDEDNESS: single
          (D) TOPOLOGY: unknown (ii) MOLECULE TYPE: protein (iii) HYPOTHETICAL: YES (v) FRAGMENT TYPE: internal (ix) FEATURE:
          (A) NAME/KEY: Domain
          (B) LOCATION: 1..24
          (D) OTHER INFORMATION: /note= "At positions 1,9,11,12, X
               is K or R; position 6, X is G or A; position 10, X
               is S or T; positions 13, 24, X is D or E; position 16,
               X is N or Q; positions 21, 23, X is L or V; other Xs,
               unspecified."

(xi) SEQUENCE DESCRIPTION: SEQ ID NO:1:

Xaa Glu Phe Xaa Xaa Xaa Xaa Gly Xaa Xaa Xaa Xaa Xaa Ala Lys Xaa
1               5                   10                  15

Ala Ala Ala Lys Xaa Ala Xaa Xaa
            20

(2) INFORMATION FOR SEQ ID NO:2:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Sense primer corresponding
               to the 5' sequences of the E3L ORF used in the
               amplification of the gene."

(iii) HYPOTHETICAL: NO (iv) ANTI-SENSE: NO (xi) SEQUENCE DESCRIPTION: SEQ ID NO:2:

TCGCGAATTC ATGGTCTAAG ATCTATATT                                        29
```

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Antisense primer
            corresponding to the 3' end of the E3L ORF used in the
            amplification of the E3L gene."

(iii) HYPOTHETICAL: NO (xi) SEQUENCE DESCRIPTION: SEQ ID NO:3:

AGGCCTGCAG TCAGAATCTA ATGATTAC                                        28

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Sense primer corresponding
            to nucleotides 1-18 of the E3L gene used in the
            amplification of E3L mutants."

(iii) HYPOTHETICAL: NO (iv) ANTI-SENSE: NO (xi) SEQUENCE DESCRIPTION: SEQ ID NO:4:

AGGCCTGCAG ATGTCTAAGA TCTATATT                                        28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Antisense primer
            corresponding to nucleotides 556-573 of the E3L
            gene used for amplifying the E3L/1-7 mutant gene."

(iii) HYPOTHETICAL: NO (iv) ANTI-SENSE: YES (xi) SEQUENCE DESCRIPTION: SEQ ID NO:5:

TCGCGAATTC TCAGAATCTA ATGATGAC                                        28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Antisense primer
            corresponding to nucleotides 535-549 of the E3L
            gene, followed by a transcription terminator, used in
            amplifying the E3L/2-2 mutant."

(iii) HYPOTHETICAL: NO (iv) ANTI-SENSE: YES (xi) SEQUENCE DESCRIPTION: SEQ ID NO:6:

TCGCGAATTC CTAAAGAAGT TTATCTAC                                                  28

(2) INFORMATION FOR SEQ ID NO:7:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Antisense primer
              corresponding to nucleotides 478-492 of the E3L
              gene, followed by a transcription terminator, used in
              amplifying the E3L/3-5 mutant."

(iii) HYPOTHETICAL: NO (iv) ANTI-SENSE: YES (xi) SEQUENCE DESCRIPTION: SEQ ID NO:7:

TCGCGAATTC CTATCCATCT GCCTTATC                                                  28

(2) INFORMATION FOR SEQ ID NO:8:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Antisense primer
              corresponding to nucleotides 400-414 of the E3L gene,
              followed by a transcription terminator, used in
              amplifying the E3L/4-5 mutant."

(iii) HYPOTHETICAL: NO (iv) ANTI-SENSE: YES (xi) SEQUENCE DESCRIPTION: SEQ ID NO:8:

TCGCGAATTC CTATTCAATA CGAAAAGA                                                  28

(2) INFORMATION FOR SEQ ID NO:9:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Sense primer corresponding
              to nucleotides 483-499 of the E3L gene used to make
              megaprimer."

(iii) HYPOTHETICAL: NO (iv) ANTI-SENSE: NO (xi) SEQUENCE DESCRIPTION: SEQ ID NO:9:

GGCAGATGHA AAATCTA                                                              17

(2) INFORMATION FOR SEQ ID NO:10:

(i) SEQUENCE CHARACTERISTICS:
          (A) LENGTH: 18 base pairs

-continued

```
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Antisense primer
                correponding to nucleotides 492-509 for E3L gene
                mutagenesis; B is T or C or G."

(iii) HYPOTHETICAL: NO (iv) ANTI-SENSE: YES (xi) SEQUENCE DESCRIPTION: SEQ ID NO:10:

AAAATCTABA CGAGATGC                                                        18

(2) INFORMATION FOR SEQ ID NO:11:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Antisense primer
                corresonding to nucleotides 513-529 of the E3L gene
                used for mutagenesis of the E3L gene; D is G or A or T."

(iii) HYPOTHETICAL: NO (iv) ANTI-SENSE: YES (xi) SEQUENCE DESCRIPTION: SEQ ID NO:11:

AAATAATGDA GCTAAAT                                                         17
```

We claim:

1. A transgenic plant resistant to an infecting virus or viroid having a dsRNA-like structure, said plant comprising a cloned DNA molecule comprising a gene encoding a vaccinia virus E3L protein and expressing said protein at a level sufficient to complex and sequester said dsRNA-like structure and to render said transgenic plant resistant to infection from said virus or viroid.

2. The transgenic plant of claim 1 which is selected from the group consisting of tobacco, potato, tomato, rice, wheat, barley, maize, cucumber, soya, sweet potato, pepper, grapes, rapeseed, sugar beet, cotton, tea, sunflower, strawberry, rose and chrysanthemum.

3. The transgenic plant of claim 1 which is selected from tobacco or potato.

4. The transgenic plant of claim 1 which is potato.

5. The tiansgenic plant of claim 1 wherein said cloned DNA molecule is introduced into said plant using an Agrobacterium transformation system.

6. The transgenic plant of claim 1 wherein said gene encoding E3L protein is natural or synthetic.

7. The transgenic plant of claim 1 wherein said gene encoding E3L protein is modified to comprise an expression enhancing modification selected from the group consisting of:

alteration of a translational initiation site located within the gene or in an inappropriate reading frame to a noninitiator codon;

insertion of a TAA termination at the end of said E3L protein gene; and utilization of plant-preferred codons.

8. The transgenic plant of claim 1 wherein said gene encoding a E3L protein is modified to contain plant-preferred codons.

9. A method of providing resistance in a tobacco plant from an infecting tobacco mosaic virus having a double-stranded RNA-like structure, said method comprising the step of transforming said tobacco plant with, a cloned DNA molecule comprising a gene encoding a vaccine virus E3L protein, such that said protein is expressed in said tobacco plant at a level sufficient to complex and sequester said dsRNA-like structure and to render said tobacco plant resistant to infection by said virus.

10. The method of claim 9 wherein said gene encoding E3L protein is natural or synthetic.

11. The method of claim 9 wherein said gene encoding E3L protein is modified to comprise an expression enhancing modification selected from the group consisting of:

alteration of a translational initiation site located within the gene or in an inappropriate reading frame to a noninitiator codon;

insertion of a TAA termination at the end of said E3L protein gene, and utilization of plant-preferred codons.

12. The method of claim 9 wherein said gene encoding a E3L protein is modified to contain plant-preferred codons.

13. A cloned DNA molecule comprising a gene encoding a E3L protein of a vaccine virus under the regulatory control of a promoter active in plant cells.

14. The cloned DNA molecule of claim 13 wherein the plant-active promoter is selected from the group consisting of the nopaline synthase promoter, the octopine synthase promoter, the Cauliflower Mosaic virus 19S promoter, the Cauliflower Mosaic virus 35S promoter and the promoter from the small subunit of ribulose bisphosphate carboxylase.

15. The cloned DNA molecule of claim 14 wherein the promoter is the Cauliflower Mosaic virus 35S promoter.

16. The cloned DNA molecule of claim 13 wherein said gene encoding a E3L protein is modified to comprise an expression enhancing modification selected from the group consisting of:
- alteration of a translational initiation site located within the gene or in an inappropriate reading frame to a noninitiator codon;

insertion of a TAA termination at the end of said E3L protein gene; and utilization of plant-preferred codons.

17. The cloned DNA molecule of claim 13 wherein said gene encoding an E3L protein is modified to contain plant-preferred codons.

18. The cloned DNA molecule of claim 13 wherein said promoter is a constitutive plant-active promoter.

* * * * *

UNITED STATES PATENT AND TRADEMARK OFFICE
CERTIFICATE OF CORRECTION

PATENT NO. : 5,990,388

DATED : Nov. 23, 1999

INVENTOR(S) : Roth et al.

It is certified that error appears in the above-identified patent and that said Letters Patent is hereby corrected as shown below:

On the title page item [56], under U.S. PATENT DOCUMENTS, please insert
--5,491,080   2/1996   Ishida ........435//172.3--.

At column 17, last line of the column, please rewrite "PCMUIV" as --pCMUIV--

At column 24, first line under "EXAMPLE 4" please rewrite "Ihibition" as --Inhibition--.

At column 26, line 36, please delete "ps" before "Nopaline Assays" and format "Nopaline Assays" as a heading.

Signed and Sealed this

Nineteenth Day of December, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,990,388
DATED : November 23, 1999
INVENTOR(S) : Roth et al.

Page 1 of 1

It is certified that error appears in the above-identified patent and that said Letters Patent is hereby corrected as shown below:

Column 3,
Lines 45 and 46, please rewrite "R/K-E-F-X-X-G/A-X-G-R/K-S-T-K-R-K/R-E/D-A-K-N/Q-A-A-A-K-L-V/V-A-L/V-D/E" as -- R/K-E-F-X-X-G/A-X-G-R/K-S/T-K/R-K/R-E/D-A-K-N/Q-A-A-A-K-L/V-A-L/V-D/E --.

Column 8,
Line 27, please rewrite "R/K-E-F-X-X-G/A-X-G-R/K-S-T-K/R-K/R-E/D-A-K-N/" as -- R/K-E-F-X-X-G/A-X-G-R/K-S/T-K/R-K/R-E/D-A-K-N/ --.

Column 13,
Line 46, please rewrite "R/K-E-F-X-X-G/A-X/G-R-K-S-T-K/R-K/R-E/D-A-K-N/" as -- R/K-E-F-X-X-G/A-X-G-R/K-S/T-K/R-K/R-E/D-A-K-N/ --.

Signed and Sealed this

Twenty-fifth Day of December, 2001

Attest:

*Attesting Officer*

JAMES E. ROGAN
*Director of the United States Patent and Trademark Office*